United States Patent
Taden et al.

(10) Patent No.: US 10,316,134 B2
(45) Date of Patent: Jun. 11, 2019

(54) ALKENYL ETHER POLYOLS

(71) Applicants: Henkel AG & Co. KGaA, Duesseldorf (DE); Max-Planck-Gesellschaft Zur Foerderung Der Wissenschaften E.V., Munich (DE)

(72) Inventors: Andreas Taden, Duesseldorf (DE); Katharina Landfester, Mainz (DE); Stefan Kirschbaum, Leverkusen (DE)

(73) Assignees: Henkel AG & Co. KGaA, Duesseldorf (DE); Max-Planck-Gesellschaft Zur Foerderung Der Wissenschaften E.V., Munich (DE)

(*) Notice: Subject to any disclaimer, the term of this patent is extended or adjusted under 35 U.S.C. 154(b) by 0 days.

(21) Appl. No.: 15/451,729

(22) Filed: Mar. 7, 2017

(65) Prior Publication Data

US 2017/0247498 A1 Aug. 31, 2017

Related U.S. Application Data

(63) Continuation of application No. PCT/EP2015/070651, filed on Sep. 9, 2015.

(30) Foreign Application Priority Data

Sep. 9, 2014 (EP) .................................. 14184099

(51) Int. Cl.
  *C08G 18/67* (2006.01)
  *C07C 217/28* (2006.01)
  (Continued)

(52) U.S. Cl.
  CPC .......... *C08G 18/6715* (2013.01); *C07C 41/03* (2013.01); *C07C 43/1785* (2013.01);
  (Continued)

(58) Field of Classification Search
  CPC . C07C 33/02; C07C 33/035; C07C 41/01–03; C07C 41/26; C07C 265/06; C07C 269/04; C07C 271/12
  See application file for complete search history.

(56) References Cited

U.S. PATENT DOCUMENTS 4,186,271 A * 1/1980 Preston ................. C07C 43/166
                                                      526/295
4,485,211 A * 11/1984 Okamoto ........... C08G 18/4862
                                                      525/349
(Continued)

FOREIGN PATENT DOCUMENTS

AU       2012219869 A1    9/2013
CN        102558491 A     7/2012
(Continued)

OTHER PUBLICATIONS

Steblyanko, A.; Choi, W.; Sanda, F.; Endo, T. Addition of Five-Membered Cyclic Carbonate with Amine and its Application to Polymer Synthesis. Journal of Polymer Science: Part A: Polymer Chemistry, vol. 38, 2375-2380. (Year: 2000).*

(Continued)

*Primary Examiner* — Michael M Dollinger
*Assistant Examiner* — Christina H Wales
(74) *Attorney, Agent, or Firm* — James E. Piotrowski

(57) ABSTRACT

The invention relates to a method for producing radiation-curable alkenyl ether polyols, to radiation-curable alkenyl ether polyols produced using the method according to the invention, and to the use thereof for the synthesis of radiation-interlinkable oligomers or polymers by means of polyaddition reactions or polycondensation reactions, in particular for the synthesis of radiation-curable polyesters, polyethers, polyurethanes and polyureas, particularly preferably UV-curable polyurethanes. The invention also relates to radiation-curable polyurethane polymers that are obtained (Continued)

by reacting at least one alkenyl ether polyol according to the invention with a polyisocyanate.

14 Claims, 5 Drawing Sheets

(51) Int. Cl.
*C08G 18/48* (2006.01)
*C08G 18/75* (2006.01)
*C08G 18/32* (2006.01)
*C07C 41/03* (2006.01)
*C07C 43/178* (2006.01)
*C08G 18/10* (2006.01)
*C08G 18/28* (2006.01)

(52) U.S. Cl.
CPC ............ *C07C 217/28* (2013.01); *C08G 18/10* (2013.01); *C08G 18/2835* (2013.01); *C08G 18/3206* (2013.01); *C08G 18/4825* (2013.01); *C08G 18/675* (2013.01); *C08G 18/755* (2013.01); *C08G 18/6795* (2013.01)

(56) References Cited

U.S. PATENT DOCUMENTS

| | | |
|---|---|---|
| 4,751,273 A | 6/1988 | Lapin et al. |
| 5,200,490 A | 4/1993 | Jaeger et al. |
| 5,384,342 A | 1/1995 | Szum |
| 5,539,014 A | 7/1996 | Swedo et al. |
| 2012/0035381 A1 | 2/2012 | Klumpe et al. |

FOREIGN PATENT DOCUMENTS

| | | |
|---|---|---|
| DE | 4109649 A1 | 9/1992 |
| JP | H07224131 A | 8/1995 |
| RU | 2100377 C1 | 12/1997 |
| WO | 2012113618 A1 | 8/2012 |

OTHER PUBLICATIONS

Steblyanko et al., Addition of Five-Membered Cyclic Carbonate with Amine and Its Application to Polymer Synthesis, Chemical Resources Laboratory, 2000, pp. 2375-2380.

M. Sangermano, N. Razza and J. V. Crivello (Macromol. Mater. Eng., 2014, 299, S. 775-793).

PEG-based Multifunctional Polyethers with Highly Reactive Vinyl-Ether Side Chains for Click-Type Functionalization; Macromolecules vol. 44, Issue: 16, pp. 6326-6334.

Kayaman-Apohan et al., Synthesis and characterization of UV-curable vinyl ether functionalized urethane oligomers, Progress in Organic Coatings 49 (2004), 23-32.

\* cited by examiner

ALKENYL ETHER POLYOLS

The present invention relates to a method for manufacturing alkenyl ether polyols as well as to alkenyl ether polyols that can be obtained by means of the method according to the invention, as well as to the use thereof for the synthesis of radiation-curable oligomers or polymers by means of polyaddition or polycondensation reactions, particularly for the synthesis of UV-curable polyesters, polyethers, polyurethanes, and polyureas, as well as the UV-curable polymers obtainable in this manner.

Cationic polymerization processes, particularly those initiated by high-energy radiation such as ultraviolet electromagnetic radiation (UV) or electron beam radiation (EB), for example, are known from the prior art and are used increasingly in industrial manufacturing processes for a multitude of products, including adhesives and glues, coating compositions, and many others. Moreover, low-energy initiation methods for cationic polymerization have also become known, for example those based on visible light. The latter-mentioned systems are currently not being used with such frequency and are still in development in part. Cationic polymerization processes are typically free of solvents, are energy-efficient, environmentally friendly, and suitable for automated process sequences. A comprehensive overview of cationic polymerization processes can be found in Matyjaszewski, K., editor, *Cationic Polymerizations: Mechanisms, Synthesis, and Applications*. (*In: Plast. Eng.* (*N. Y.*), 1996; 35, Dekker). An overview of UV-curing cationic polymerization is given, for example, by M. Sangermano, N. Razza and J. V. Crivello (Macromol. Mater. Eng., 2014, 299, pp. 775-793). Among the commonly recognized advantages of cationic polymerization are particularly the tolerance of (atmospheric) oxygen as well as the possibility of a continuous reaction after initiation. In the relevant literature, this behavior is also referred to as "dark curing" and refers to the continuing curing of the polymerizable material after shock-initiation, for example through UV, EB, or a heat surge, including in the absence of electromagnetic radiation, electron beams, or increased heat input. This dark curing process is especially advantageous for a multitude of technical joining processes.

In general, these methods compete with radical chain polymerization processes initiated by electromagnetic or EB radiation, the output—and hence applicability—of which suffers from the oxygen-sensitive nature of the mechanism of radical polymerization.

In relation to cationic polymerization, alkenyl ethers are known for their high reactivity and are therefore used as monomeric precursors. The alkenyl ether-functionalized monomeric precursors have a series of advantages: Due to their high reactivity, they crosslink quickly, tend to be odor-neutral, and have good durability and adhesive characteristics. As a result of the high reactivity, they can also tolerate a multitude of functional groups to a large extent, such as urethane groups, for example, and are destroyed less easily by side reactions in the polymerization.

Epoxides and oxetanes are also suitable reactive precursors for cationic polymerization processes but often require a thermal "push" after the actual initialization in order to increase the polymerization rate and output. While epoxides and oxetanes are among the most reactive cationically polymerizable compounds, the reaction is disrupted or even brought to a standstill by a greater variety of functional groups. It is known, for instance, that cationic polymerization or crosslinking tends to come to a standstill prematurely in the presence of urethane groups in the case of epoxides and oxetanes.

It has been generally observed that low-molecular (radiation-curable) compounds, regardless of whether they are radically and/or cationically polymerizable, cannot be considered for many applications or have substantial drawbacks. Due to their low molecular weight, such compounds often already have an appreciable vapor pressure at low temperatures and can therefore act as "volatile organic compounds" (VOC). The volatility of the substances is problematic in terms of the contamination of the environment (emissions through vaporization) and various health- and safety-related concerns (resorption via respiratory tract, skin, digestion, etc./formation of ignitable mixtures,/etc.). Another substantial limitation is the lack of adjustability of the rheological or mechanical characteristics of such low-molecular materials before the actual curing.

For this reason, oligomers or polymers are usually used in the prior art, thereby working around to a large extent the problems brought about by vapor pressure or application viscosity. Polyurethanes and polyurethane prepolymers (PU), which can be set over a wide range of characteristics and are functionalized by radically reactive groups, are widely used in this context. The most common is a preferably terminal functionalization by means of acrylate or methacrylate groups. The corresponding materials are often referred to by the abbreviations PUA or PUMA. One drawback of these compounds is the fundamentally associated air- or oxygen-sensitive crosslinking reaction. Another noteworthy drawback are the low degrees of crosslinking, particularly when using linear, terminally functionalized PUA or PUMA compounds.

Moreover, terminally functionalized alkylene ether-functionalized oligomers or polymers are known from the prior art which can be polymerized cationically and are not subject to any oxygen inhibition. The corresponding fully polymerized systems tend to exhibit a lower crosslink density, since it is typically only the terminals groups that react with one another. The mechanical characteristics of the desired polymer or of the corresponding polymer-containing product can therefore be influenced only under certain conditions and within a certain framework.

A need therefore exists for a system that has been improved in relation to the prior art and can provide high crosslink densities through cationic polymerization. This system should also have a barely noticeable vapor pressure, that is, it should not fall under the current VOC directives, and should enable the adjustment of rheological and mechanical characteristics over a wide range already before the cationic polymerization and thus adaptation to a multitude of applications.

As a result of the high crosslink density to be achieved, the mechanical characteristics of the corresponding polymers and of the polymer-containing products, such as adhesives and glues, as well as coating compositions, can be influenced to the effect that they, as required, deviate more or less drastically from the mechanical characteristics of the prepolymers used.

It was found that alkenyl ether-functionalized polyols constitute outstanding precursors for numerous cationically polymerizable compounds that can particularly be manufactured through polycondensation and polyaddition reactions. Depending on their structure and degree of functionalization, these cationically polymerizable compounds, in turn, enable good control of the crosslink density in the resulting polymeric systems after cationic curing.

The alkenyl ether polyols manufactured according to the invention can be used as starting materials for the synthesis of oligomers and polymers that are accessible by way of polyaddition processes or polycondensation reactions. Polymers that can be obtained in this manner include polyesters, polyethers, polyurethanes, and polyureas, for example. The alkenyl ether functionalities enable additional functionalization, crosslinking and polymerization reactions, for example cationic polymerization or even radical copolymerization, of the polyols and their reaction products. Other noteworthy examples are thiol-ene addition or also acetal formation.

In particular, the alkenyl ether-functionalized polyols enable the synthesis of novel polyurethane structures that can be crosslinked in subsequent cationic polymerization mechanisms under the effect of electromagnetic radiation, particularly UV radiation, or the effect of EB. In the description that follows, no explicit distinction will be made any longer between electromagnetic radiation and EB radiation; instead, the term "UV" will be used as a synonym for radiation that is capable of initiation. It is self-evident, however, that radiation other than UV radiation that is capable of initiation can also be used in the embodiments described. Such embodiments also fall within the scope of the present invention.

A first object of the present invention is therefore a method for manufacturing an alkenyl ether polyol containing at least one alkenyl ether group, particularly a 1-alkenyl ether group, and at least two hydroxyl groups (—OH), through
A) Conversion of an alkenyl ether containing at least one alkenyl ether group and at least one functional group selected from among —OH, —COOH, —SH, —NH$_2$ and derivatives thereof,
with (i) an epoxide or (ii) a cyclic carbonate or derivative thereof; or
B) Conversion of an alkenyl ether containing at least one alkenyl ether group and at least one functional group selected from (i) epoxide groups and (ii) cyclic carbonate groups or derivatives thereof,
with an alcohol, thiol, a carboxylic acid, or an amine or derivative of the above.

Moreover, the present invention relates to alkenyl ether polyols of formula (I) or (V),

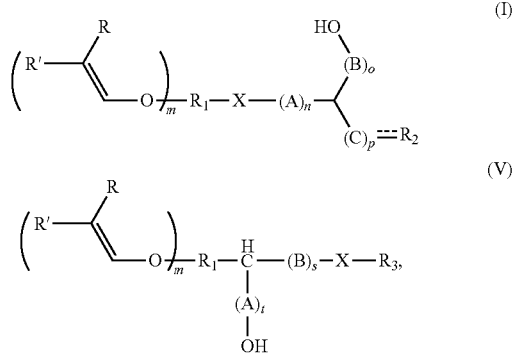

where
R$_1$ is an at least divalent organic residue, particularly an at least divalent linear or branched, substituted or unsubstituted alkyl with 1 to 20 carbon atoms or linear or branched, substituted or unsubstituted heteroalkyl with 1 to 20 carbon atoms and at least one oxygen or nitrogen atom, R$_2$ is an organic residue, optionally with at least one —OH group and/or 1 to 1000 carbon atoms, particularly an optionally divalent or polyvalent, linear or branched, substituted or unsubstituted alkyl with 1 to 20 carbon atoms or linear or branched, substituted or unsubstituted heteroalkyl with 1 to 20 carbon atoms and at least one oxygen or nitrogen atom, R$_3$ is an organic residue, optionally with 1 to 1000 carbon atoms, particularly an optionally divalent or polyvalent, linear or branched, substituted or unsubstituted alkyl

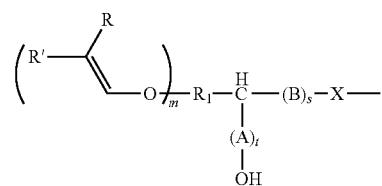

with 1 to 20 carbon atoms or linear or branched, substituted or unsubstituted heteroalkyl with 1 to 20 carbon atoms and at least one oxygen or nitrogen atom, or a (poly)alkylene glycol of the formula —O—[CHR$_a$-CH$_2$O]$_b$—R$_b$, where R$_a$ is H or a C$_{1-4}$ alkyl residue, R$_b$ is OH or
and b is 1 to 100, in formula (I), X stands for O, S, C(=O)O, OC(=O)O, C(=O)OC(=O)O, NR$_x$, NR$_x$C(=O)O, NR$_x$C(=O)NR$_x$ or OC(=O)NR$_x$, in formula (V), X stands for O, S, OC(=O), OC(=O)O, OC(=O)OC(=O), NR$_z$, NR$_z$C(=O)O, NR$_z$C(=O)NR$_z$ or OC(=O)NR$_z$, each R and R' is selected independently from among H, C$_{1-20}$ alkyl, and C$_{2-20}$ alkenyl, particularly with one of R and R' being H and the other being C$_{1-4}$ alkyl, or both being H, each A, B, and C is independently selected from among CR"R'", R" and R'" are selected independently from among H, a functional group, such as —OH, —NH$_2$, —NO$_2$, —CN, —OCN, —SCN, —NCO, —SCH, —SH, —SO$_3$H or SO$_2$H, for example, and an organic residue, particularly H and C$_{1-20}$ alkyl, or R" and R'" together or with the carbon atom to which they are bonded are an organic residue, or two of R" and R'" that are bonded to neighboring carbon atoms form a bond together in order to form a double bond between the neighboring carbon atoms, ═══ is a single or double bond, and if it is a double bond, the carbon atom that is bonded to R$_2$ bears only one substituent R" or R'", m is an integer from 1 to 10, preferably 1,
n, p and o are each 0 or an integer from 1 to 10, where n+p+o=1 or more, particularly 1 or 2,
s and t are each 0 or an integer from 1 to 10, where s+t=1 or more, particularly 1 or 2, R$_x$ is H, an organic residue, or

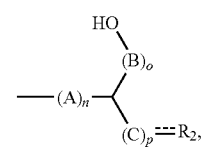

and if X is not NR$_x$ where R$_x$=

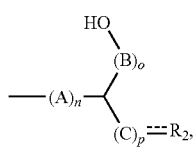

$R_2$ has at least one substituent that is selected from among —OH and

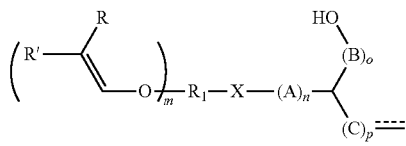

and
$R_z$ H is an organic residue or

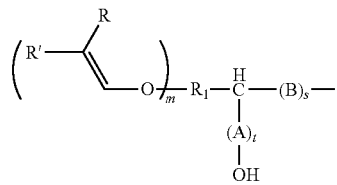

and if X is not $NR_z$ where $R_z$=

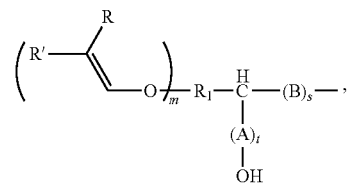

$R_3$ has at least one substituent that is selected from among —OH and

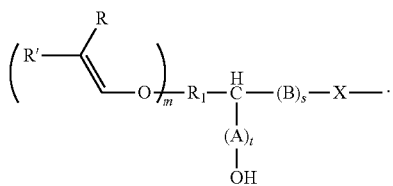

The present invention further relates to alkenyl ether polyols, particularly those of formula (I) or (V) that can be obtained using a method according to the present invention.

Another aspect of the invention relates to the use of the alkenyl ether polyols described herein for the synthesis of UV-curable oligomers or polymers by means of polyaddition or polycondensation reactions, particularly for the synthesis of UV-curable polyesters, polyethers, polyurethanes, and polyureas, especially preferably UV-curable polyurethanes and corresponding methods.

Finally, another aspect of the present invention concerns a UV-curable polymer that can be obtained according to the above-described use/methods, particularly to a UV-curable polyurethane polymer that can be obtained through conversion of at least one alkenyl ether polyol of the present invention with a polyisocyanate.

As used herein, "alkenyl ether polyol" refers to compounds containing at least one group of the formula —O alkenyl and at least two hydroxy groups. It is preferred that the alkenyl ether polyol comprise an organic residue to which both the alkenyl ether group and the hydroxy groups are bonded; that is, the hydroxy groups are preferably not bonded to the alkenyl group. It is also preferred that the alkenyl ether group be a 1-alkenyl ether group, that is, that the C—C double bond be adjacent to the oxygen atom.

As used herein, the term "alkyl" refers to a linear or branched, unsubstituted or substituted saturated hydrocarbon residue, particularly residues of the formula $C_nH_{2n+1}$. Examples of alkyl residues include but are not limited to methyl, ethyl, n-propyl, iso-propyl, n-butyl, 2-butyl, tert-butyl, n-pentyl, n-hexyl and the like. As used herein, "heteroalkyl" refers to alkyl residues in which at least one carbon atom is replaced by a heteroatom, such as particularly oxygen, nitrogen, or sulfur. Examples include but are not limited to ethers and polyethers, such as diethyl ether, polyethylene oxide, polypropylene oxide, or polytetramethylene oxide.

As used herein, the term "alkenyl" refers to a linear or branched, unsubstituted or substituted hydrocarbon residue containing at least one C—C double bond.

As used herein particularly in connection with alkyl and heteroalkyl groups, "substituted" refers to compounds in which one or more carbon and/or hydrogen atoms are replaced by other atoms or groups. Suitable substituents include but are not limited to —OH, —NH$_2$, —NO$_2$, —CN, —OCN, —SCN, —NCO, —SCH, —SH, —SO$_3$H, SO$_2$H, —COOH, —CHO and the like.

The term "organic residue" as used herein refers to any organic residue that contains carbon atoms. Organic residues can be derived particularly from hydrocarbons, and any carbon and hydrogen atom can be replaced by other atoms or groups. Organic residues in terms of the invention contain 1 to 1000 carbon atoms in various embodiments.

"Epoxide" as used herein refers to compounds containing an epoxide group.

As used herein, "cyclic carbonate" refers to cyclic compounds that contain the group —O—C(=O)—O— as a ring component.

The term "alcohol" refers to an organic compound that contains at least one hydroxyl group (—OH).

The term "amine" refers to an organic compound that comprises at least one primary or secondary amino group (—NH$_2$, —NHR).

The term "thiol" or "mercaptan" refers to an organic compound that contains at least one thiol group (—SH).

The term "carboxylic acid" refers to a compound that contains at least one carboxyl group (C(=O)OH).

As used herein, the term "derivative" refers to a chemical compound that has been altered in relation to a reference compound by one or more chemical reactions. In connection with the functional groups —OH, —COOH, —SH and —NH$_2$ as well as the classes of compounds of the alcohols, carboxylic acids, thiols, and amines, the term "derivative" particularly includes the corresponding ionic groups/compounds and salts thereof, i.e., alcoholates, carboxylates, thiolates, and ammonium (quaternary nitrogen) compounds. In connection with the cyclic carbonates, the term "derivative" particularly includes the thio derivatives of the carbonates described more precisely below, i.e., compounds in which one, two, or all three oxygen atoms of the group O—C(=O)—O— have been replaced by sulfur atoms.

As used herein in conjunction with a numerical value, the term "at least" refers to exactly that numerical value or greater. "At least one" therefore refers to 1 or more, i.e., 2, 3, 4, 5, 6, 7, 8, 9, 10, or more. In connection with a type of compound, the term refers not to the absolute number of molecules, but rather to the number of the types of substances that fall under the respective collective term. For example, "at least one epoxide" therefore means that at least one type of epoxide but also several different epoxides can be contained.

As used herein, the term "curable" refers to a change in the state and/or structure in a material as a result of a chemical reaction that is usually but not necessarily induced by at least one variable, such as time, temperature, moisture, radiation, presence and quantity of a catalyst or accelerant or the like which promotes curing. The term refers both to the complete and partial curing of the material. "UV-curable" or "UV-crosslinkable" therefore refer to compounds that react chemically to exposure to UV and form new (intra- or intermolecular) bonds.

The term "divalent" or "2-valent" as used herein in connection with residues or groups refers to a residue or a group that has at least two points of attachment that produce a compound with other moieties. In terms of the present invention, a divalent alkyl residue therefore refers to a residue of the formula -alkyl-. Such a divalent alkyl residue is also referred to herein as an alkylenyl residue. Accordingly, "polyvalent" means that a residue or a group possesses more than one point of attachment. For example, such a residue can also be trivalent, tetravalent, pentavalent, or hexavalent. "At least divalent" therefore means divalent or greater.

The term "poly" refers to a repeating unit of a (functional) group or structural unit that follows this prefix. For instance, "polyol" refers to a compound with at least 2 hydroxy groups, and "polyalkylene glycol" refers to a polymer composed of alkylene glycol monomer units.

"Polyisocyanate," as used herein, refers to organic compounds that contain more than one isocyanate group (—NCO).

The alkenyl ethers can be aliphatic compounds which, in addition to the alkenyl ether group(s), contain at least one other functional group that is reactive to epoxy or cyclocarbonate groups, including —OH, —COOH, —SH, NH$_2$ and derivatives thereof. The functional groups attack the ring carbon of the epoxide ring or the carbonyl carbon atom of the cyclocarbonate nucleophilically, upon which the ring opens and a hydroxyl group is formed. Depending on the reactive, nucleophilic group, an O—C—, N—C, S—C, or O—/N—/S—C(=O)O bond is attached.

According to the method described herein, the alkenyl ether polyol can be manufactured via two alternative routes A) and B).

In route A), an alkenyl ether containing the at least one alkenyl ether group and at least one functional group selected from among —OH, —COOH, —SH, —NH$_2$ and derivatives thereof is converted with (i) an epoxide or (ii) a cyclic carbonate or derivative thereof.

In route B), an alkenyl ether containing at least one alkenyl ether group and at least one functional group selected from among (I) epoxide groups and (ii) cyclic carbonate groups or derivatives thereof is converted with an alcohol, thiol, a carboxylic acid, or an amine or derivative of the above.

Independently of the route, the alkenyl ether polyols are formed through reaction of the hydroxy, thiol, carboxyl, or amino groups with an epoxide or cyclic carbonate group under opening of the ring.

In all embodiments of the invention, the reaction partners are selected such that the reaction product, i.e., the alkenyl ether polyol obtained, bears at least two hydroxyl groups.

In various embodiments, the alkenyl ether polyol is manufactured through conversion of an alkenyl ether containing at least one alkenyl ether group and at least one functional group selected from among —OH, —COOH, —SH, —NH$_2$ and derivatives thereof with (i) an epoxide or (ii) a cyclic carbonate or derivative thereof, with the alkenyl ether polyol manufactured in this manner being an alkenyl ether polyol of formula (I)

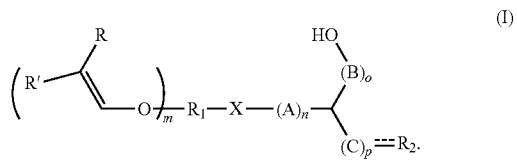

In the compounds of formula (I),

R$_1$ is an at least divalent organic residue, optionally with 1 to 1000 carbon atoms, particularly an at least divalent linear or branched, substituted or unsubstituted alkyl with 1 to 50, preferably 1 to 20 carbon atoms, or a linear or branched, substituted or unsubstituted heteroalkyl with 1 to 50, preferably 1 to 20 carbon atoms, and at least one oxygen or nitrogen atom, R$_2$ is an organic residue, optionally with at least one OH group and/or 1 to 1000 carbon atoms, particularly an (optionally divalent or polyvalent) linear or branched, substituted or unsubstituted alkyl with 1 to 50, preferably 1 to 20 carbon atoms, or a linear or branched, substituted or unsubstituted heteroalkyl with 1 to 50, preferably 1 to 20 carbon atoms, and at least one oxygen or nitrogen atom. However, R$_2$ can also be a high-molecular residue such as a polyalkylene glycol, for example. Such a (poly)alkylene glycol can have the formula —O—[CHR$_a$CH$_2$O]$_b$—R$_b$, for example, where R$_a$ is H or a C$_{1-4}$ alkyl residue, R$_b$ is H or an organic residue, and b is 1 to 100.

In the compounds of formula (I), X is O, S, C(=O)O, OC(=O)O, C(=O)OC(=O)O, NR$_x$, NR$_x$C(=O)O, NR$_x$C(=O)NR$_x$ or OC(=O)NR$_x$. In preferred embodiments, X is O, OC(=O)O, NR$_x$ or NR$_x$C(=O)O.

Each R and R' is selected independently from among H, C$_{1-20}$ alkyl, and C$_{2-20}$ alkenyl, particularly with one of R and R' being H and the other being C$_{1-4}$ alkyl, or both being H. Especially preferably, R is H and R' is H or —CH$_3$.

Each A, B, and C is selected independently from among CR"R"', with R" and R"' being selected independently from among H, a functional group such as —OH, —NH$_2$, —NO$_2$, —CN, —OCN, —SCN, —NCO, —SCH, —SH, —SO$_3$H, or SO$_2$H, for example, and an organic residue. In particular, R" and R"' are independently H or C$_{1-20}$ alkyl. However, R" and R"' can, either together or together with the carbon atom to which they are bonded, also form an organic residue, including cyclic residues, or a functional group. Examples of such residues are =CH$_2$, =CH-Alkyl or =C(alkyl)$_2$, =O, =S, —(CH$_2$)$_{aa}$— where aa=3 to 5 or derivatives thereof, in which one or more methylene groups are replaced by heteroatoms such as N, O, or S. However, two of R" and R"' that are bonded to neighboring carbon atoms can also form a bond together. As a result, a double bond is formed between the two neighboring carbon atoms (i.e., C(R")═C(R"')—).

═ stands for a single or double bond. If it stands for a single or double bond, the carbon atom that is bonded to $R_2$ bears only one substituent R" or R"'.

In the compounds of formula (I), m is an integer from 1 to 10, preferably 1 or 2, especially preferably 1. That is, the compounds preferably bear only 1 or 2 alkenyl ether group(s).

n, p, and o are each 0 or an integer from 1 to 10. They meet the condition n+p+o=1 or more, particularly 1 or 2. It is especially preferred that n or o be 1 and the others 0. Alternatively, it is especially preferred that n or o be 2 and the others 0. It is also preferred that p be 0 and one or n and o be 1 or 2 and the other 0. Embodiments in which n and o are 1 and p is 0 are also preferred.

$R_x$ is H, an organic residue, or

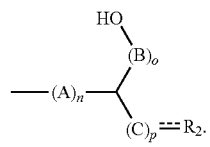

In order for the alkenyl ether polyol to have at least two hydroxyl groups, the compound of formula (I) also meets the condition that, if X is not $NR_x$ where

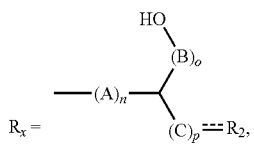

$R_2$ has at least one substituent that is selected from among —OH and

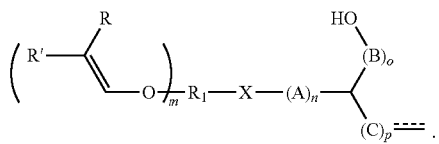

The second hydroxyl group of the compound of formula (I) is therefore either contained as a substituent in the organic residue $R_2$ or X contains another residue of formula

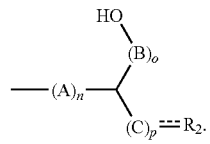

In various embodiments of the method according to the invention for manufacturing an alkenyl ether polyol, the alkenyl ether, which contains at least one alkenyl ether group and at least one functional group selected from among —OH, —COOH, —SH, $NH_2$ and derivatives thereof, is an alkenyl ether of formula (II).

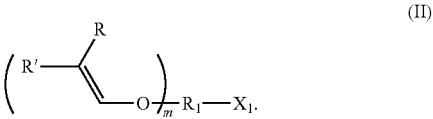

Such an alkenyl ether can be used, for example, to synthesize an alkenyl ether polyol of formula (I) through conversion thereof with an epoxide or a cyclic carbonate.

In the compounds of formula (II), $R_1$, R, R', and m are defined as above for formula (I). In particular, the preferred embodiments of $R_1$, R, R', and m described above for the compounds of formula (I) can be applied in like manner to the compounds of formula (II).

In the compounds of formula (II), $X_1$ is a functional group selected from among OH, —COOH, —SH, —$NHR_y$, and derivatives thereof, and $R_y$ is H or an organic residue, preferably H.

The derivatives of the functional groups —OH, —COOH, —SH, —$NHR_y$, are preferably the ionic variants already described above in connection with the definition of the term, which are produced through the removal or bonding of a proton, here particularly the alcoholates, thiolates, and carboxylates, very especially preferably the alcoholates.

Especially preferably, $X_1$ is —OH or —O⁻ or —$NH_2$.

An especially preferred embodiment of the method according to the invention is characterized in that m is 1, $X_1$ —OH, or —$NH_2$, preferably —OH, $R_1$ is a divalent, linear or branched $C_{1-10}$ alkyl residue (alkylenyl residue), particularly ethylenyl, propylenyl, butylenyl, pentylenyl or hexylenyl, and one of R and R' is H and the other is H or —$CH_3$.

The alkenyl ethers that can be used in relation to the present invention, particularly those of formula (II), can be reaction products of various optionally substituted alkanols (monoalcohols and polyols) with acetylene, for example. Specific examples include but are not limited to 4-hydroxybutyl vinyl ether (HBVE); 2-hydroxybutyl vinyl ether; 2-(hydroxyethoxy)ethyl vinyl ether; ethylene glycol monovinyl ether; propylene glycol monovinyl ether, 1,4-cyclohexanedimethanol monovinyl ether, and 3-aminopropyl vinyl ether.

Another embodiment of the method according to the invention is characterized in that the epoxide that is converted with the alkenyl ether is an epoxide of formula (III) or (IIIa)

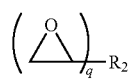

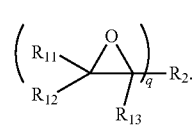

In compounds of formulas (III) and (IIIa), $R_2$ is as defined above for formula (I).

$R_{11}$, $R_{12}$, and $R_{13}$, independently of one another, are H or an organic residue, optionally with at least one —OH group, particularly a linear or branched, substituted or unsubstituted alkyl with 1 to 20 carbon atoms or linear or branched, substituted or unsubstituted heteroalkyl with 1 to 20 carbon atoms and at least one oxygen or nitrogen atom.

q is an integer from 1 to 10, preferably 1 or 2.

Accordingly, epoxy compounds that can be used in the methods according to the invention for the manufacture of alkenyl ether polyols are preferably linear or branched, substituted or unsubstituted alkanes with 1 to 1000, preferably 1 to 50 or 1 to 20 carbon atoms that bear at least one epoxy group. Optionally, these epoxy compounds can additionally bear one or more hydroxy groups, as a result of which the degree of hydroxyl functionalization of the alkenyl ether polyol resulting from the reaction of an alkenyl ether that is reactive to epoxides with an epoxide, as described above, is high. In later polymerization reactions, in turn, the crosslink density of the desired polymer can thus be controlled.

During the reaction of an alkenyl ether compound (alkenyl ether with at least one functional group selected from among —OH, —COOH, —SH, NH$_2$ and derivatives thereof), an alcohol is produced under ring-opening of the epoxide. In terms of the present invention, the alcoholic group is thus "regenerated" over the course of the bonding from the reactions of a first alcohol or a compound that is chemically related in this context (amine, thiol, carboxylic acid, etc.) with an epoxide.

In various embodiments, the epoxy compound can bear more than one epoxy group. This enables the conversion of such an epoxy compound with more than one alkenyl ether compound that is reactive to epoxides, such as an aminoalkenyl ether or hydroxyalkenyl ether.

In especially preferred embodiments, the epoxide is an epoxide of formula (III), where q is 1 or 2, and if q is 2, R$_2$ is —CH$_2$—O—C$_{1-10}$-alkylenyl-O—CH$_2$—, and if q is 1, R$_2$ is —CH$_2$—O—C$_{1-10}$-alkyl.

Examples of epoxy compounds that can be used in the manufacturing methods according to the invention are particularly glycidyl ethers, such as but not limited to 1,4-butanediol diglycidyl ether (BDDGE); neopentyl diglycidyl ether; cyclohexane dimethanol diglycidyl ether; hexanediol diglycidyl ether, polypropylene glycol diglycidyl ether; polyethylene glycol diglycidyl ether; mono-, di- or triglycidyl ethers of ethyoxylated or propoxylated glycerin and isopropyl glycidyl ether (IPGE).

In various embodiments, the alkenyl ether polyol of formula (I) can be obtained through conversion of an alkenyl ether of formula (II) with an epoxide of formula (III) or (IIIa).

Instead of an epoxide, the compounds that are converted with the compounds that are reactive to epoxides (alkenyl ether compounds) can also be cyclic carbonates or derivatives thereof. In terms of the present invention, cyclic carbonate compounds having a similar reactivity as the epoxides to the compounds used as reaction partners that add both epoxides and cyclic carbonate compounds under ring-opening and "regeneration" of an alcoholic functional group nucleophilically on the methylene of the epoxide ring in the case of an epoxide or on the carbonyl carbon atom in the case of a cyclic carbonate, as a result of which an O—C—, N—C, S—C, or O—/N—/S—C(=O)O bond is formed depending on the reactive, nucleophilic residue.

In preferred embodiments, the cyclic carbonates that can be converted in the method according to the invention with an alkenyl ether, particularly an alkenyl ether of formula (II), are ethylene carbonates of formula (IV) or (IVa).

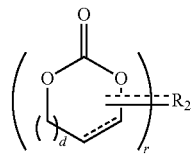

(IVa)

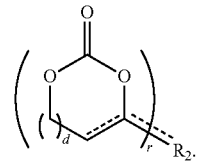

(IV)

In compounds of formulas (IV) and (IVa), R$_2$ is as defined above for formulas (I), (III), and (IIIa). In particular, R$_2$ is a C$_{1-10}$ hydroxy alkyl. In other embodiments, R$_2$ can be =CH$_2$.

═ is a single or double bond, preferably a single bond. As will readily be understood, if the ring contains a double bond, R$_2$ is bonded not via an exo double bond but rather via a single bond, and vice versa.

d is 0, 1, 2, 3, 4, or 5, preferably 0 or 1, especially preferably 0, and r is an integer from 1 to 10, preferably 1 or 2, very especially preferably 1.

If d is 1—that is, if the cyclocarbonate is a 1,3-dioxane-2-on—R$_2$ can be in the 4 or 5 position but is preferably in the 5 position.

Examples of cyclic carbonates include but are not limited to 1,3-dioxolane-2-on, 4,5-dehydro-1,3-dioxolane-2-on, 4-methylene-1,3-dioxolane-2-on, and 1,3-dioxane-2-on that are substituted in the 4 or 5 position with R$_2$.

In various embodiments of the invention, cyclic carbonates are used that are derivatives of the carbonates of formulas (IV) and (IVa). Examples of derivatives include those which are substituted at the ring methylene groups not bearing the R$_2$ residue, for example with organic residues, particularly linear or branched, substituted or unsubstituted alkyl or alkenyl residues with up to 20 carbon atoms, particularly =CH$_2$ and —CH=CH$_2$, or linear or branched, substituted or unsubstituted heteroalkyl or heteroalkenyl residues with up to 20 carbon atoms and at least one oxygen or nitrogen atom, or functional groups such as —OH or —COOH, for example. Examples of such derivatives include 4-methylene-1,3-dioxolane-2-on, which bears the R$_2$ residue at the 5 position.

In various embodiments in which the R$_2$ residue is bonded by a single bond, the ring carbon atom bearing the R$_2$ residue can be substituted by another substituent that is defined like the abovementioned substituents for the other ring methylene group.

Other derivatives are those in which one or both of the ring oxygen atoms are replaced by sulfur atoms as well as those in which, alternatively or in addition, the carbonyl oxygen atom is replaced by a sulfur atom. One especially preferred derivative is 1,3-oxathiolane-2-thione.

In various embodiment, the cyclic carbonate is 4-methylene-1,3-dioxolane-2-on bearing the R$_2$ residue at the 5 position. When such a cyclic carbonate is converted with an alkyl ether that bears an amino group as a reactive group, a compound of formula (Ia) can be formed:

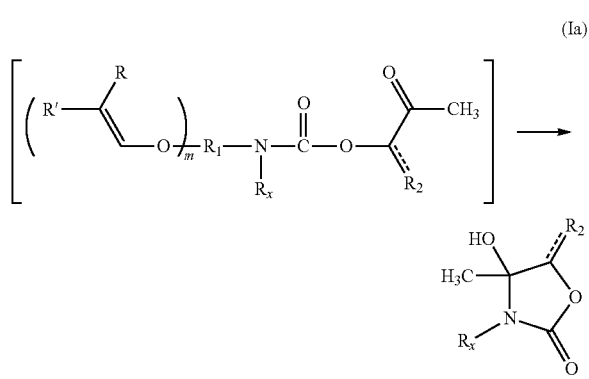

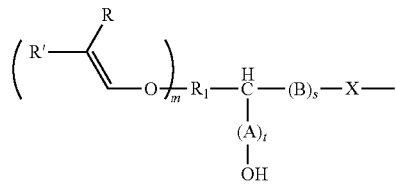

and b is 1 to 100.

In the compounds of formula (V), X is O, S, OC(=O), OC(=P)O, OC(=O)OC(=O), $NR_z$, $NR_zC(=O)O$, $NR_zC(=O)NR_z$, or $OC(=O)NR_z$. In preferred embodiments, X is O, OC(=O)O, $NR_z$, or $OC(=O)NR_z$.

Each R and R' is selected independently from among H, $C_{1-20}$ alkyl, and $C_{2-20}$ alkenyl, particularly with one of R and R' being H and the other being $C_{1-4}$ alkyl, or both being H. Especially preferably, R is H and R' is H or —$CH_3$.

Each A and B is selected independently from among CR"R'", with R" and R'" being selected independently from among H, a functional group such as —OH, —$NH_2$, —$NO_2$, —CN, —OCN, —SCN, —NCO, —SCH, —SH, —$SO_3H$ or $SO_2H$, for example, and an organic residue. In particular, R" and R'" are independently H or $C_{1-20}$ alkyl. However, R" and R'" can, either together or together with the carbon atom to which they are bonded, also form an organic residue, including cyclic residues, or a functional group. Examples of such residues are =$CH_2$, =CH-Alkyl or =$C(alkyl)_2$, =O, =S, —$(CH_2)_{aa}$— where aa=3 to 5 or derivatives thereof, in which one or more methylene groups are replaced by heteroatoms such as N, O, or S. However, two of R" and R'" that are bonded to neighboring carbon atoms can also form a bond together. As a result, a double bond is formed between the two neighboring carbon atoms (i.e., C(R")=C(R'")—).

In the compounds of formula (V), m is an integer from 1 to 10, preferably 1 or 2, especially preferably 1. That is, the compounds preferably bear only 1 or 2 alkenyl ether group(s).

s and t are each 0 or an integer from 1 to 10. They meet the condition s+t=1 or more, particularly 1 or 2. It is especially preferred that s or t be 1 and the other 0.

$R_z$ is H, an organic residue or

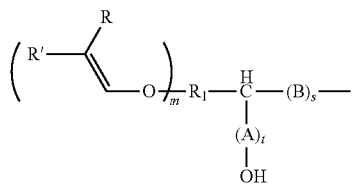

In order for the alkenyl ether polyol of formula (V) to meet the condition that it bear at least two hydroxyl groups, if X is not $NR_z$ where $R_z$=

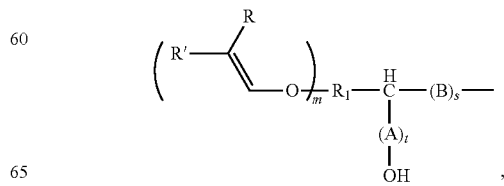

In this compound, m, $R_1$, R, R', $R_2$, and $R_x$ are as defined above for the compounds of formulas (I)-(IV).

In various embodiments, during the conversion of the aforedescribed cyclocarbonates and derivatives thereof of formulas (IV) and (IVa) with a compound of formula (II), (i) $X_1$ is —$NH_2$ or a derivative thereof, and q or r is 1; or (ii) $X_1$ is —OH or a derivative thereof, and q or r is 2.

In other embodiments, the alkenyl ether polyol can be obtained through conversion of the compounds listed in route B). In route B), the alkenyl ether is manufactured through conversion of an alkenyl ether containing at least one alkenyl ether group and at least one functional group selected from among (i) epoxide groups and (ii) cyclic carbonate groups or derivatives thereof with an alcohol, thiol, a carboxylic acid, or an amine or derivative of the above.

In various embodiments of this method, the alkenyl ether polyol is an alkenyl ether polyol of formula (V)

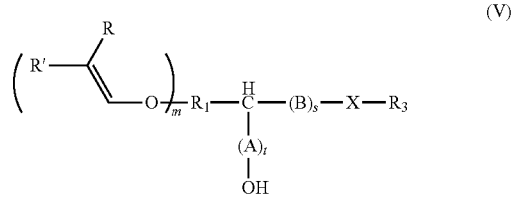

In the compounds of formula (V). $R_1$ is as defined above for the compounds of formula (I).

$R_3$ is an organic residue, optionally with at least one OH group and/or 1 to 1000 carbon atoms, particularly an (optionally divalent or polyvalent) linear or branched, substituted or unsubstituted alkyl with 1 to 50, preferably 1 to 20 carbon atoms, or a linear or branched, substituted or unsubstituted heteroalkyl with 1 to 50, preferably 1 to 20 carbon atoms, and at least one oxygen or nitrogen atom. However, $R_2$ can also be a high-molecular residue such as a polyalkylene glycol, for example. Such a (poly)alkylene glycol can have the formula —O—[$CHR_aCH_2O$]$_b$—$R_b$, for example, where $R_a$ is H or a $C_{1-4}$ alkyl residue, $R_b$ is H or an organic residue, or $R_3$ is substituted with at least one substituent that is selected from among —OH and

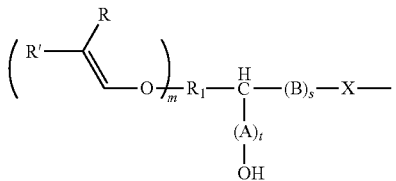

In other preferred embodiments, the method according to the invention is characterized in that the alkenyl ether, which contains at least one alkenyl ether group and at least one functional group selected from among (I) epoxide groups and (ii) cyclic carbonate groups or derivatives thereof, is an alkenyl ether of formula (VI) or (VII)

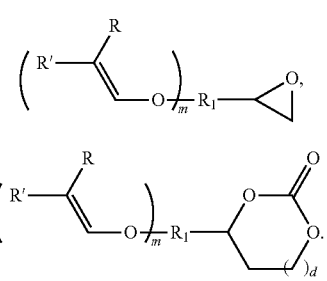

In the compounds of formula (VI) or (VII), R, R', and m are as defined above for the compounds of formulas (I) and (II).

d is as defined above for formulas (IV) and (IVa); that is, d is 0, 1, 2, 3, 4, or 5, preferably 0 or 1, especially preferably 0.

In especially preferred embodiments, $R_1$ is $C_{1-10}$-alkylenyl-O—$CH_2$— in the alkenyl ethers of formula (VI) or (VII).

The epoxy group-bearing alkenyl ethers of formula (VI) can be substituted on the epoxy residue, i.e., the methylene groups of the oxirane ring can, as shown in formula (IIIa), be substituted with $R_{11}$-$R_{13}$.

In various embodiments, the alkenyl ethers of formula (VII) are substituted on the cyclocarbonate ring or the cyclocarbonate ring is substituted by a corresponding derivative. Suitable substituted cyclocarbonates as well as derivatives thereof are those which were described above in connection with formulas (IV) and (IVa). In particular, the cyclocarbonate residue is preferably a 1,3-dioxolane-2-on or 1,3-dioxane-2-on residue, which can be optionally substituted, for example with a methylene group.

Suitable compounds of formula (VI) include but are not limited to vinyl glycidyl ether and 4-glycidyl butyl vinyl ether (GBVE), with the latter being obtainable through conversion of 4-hydroxybutyl vinyl ether with epichlorohydrin.

Suitable compounds of formula (VII) include but are not limited to 4-(ethenyloxy methyl)-1,3-dioxolane-2-on, which can be obtained through transesterification of glycerin carbonate with ethyl vinyl ether.

In various embodiments, the alkenyl ether, which contains at least one alkenyl ether group and at least one functional group selected from among (I) epoxide groups and (ii) cyclic carbonate groups or derivatives thereof, particularly one of formula (VI) or (VII), is converted with an alcohol. The alcohol can be a diol or polyol or a corresponding alcoholate. In particular, the alcohol can be a polyalkylene glycol of the formula HO—[$CHR_a CH_2 O$]$_b$—H, where $R_a$ is H or a $C_{1-4}$ alkyl residue and b is 1 bis 100, particularly 1 to 10.

Route B) therefore represents an alternative embodiment of the present invention in which the epoxide or the cyclic carbonate compounds (for example, ethylene carbonate or trimethylene carbonate compounds) have at least one or more alkenyl ether groups. The conversion of these epoxide or cyclic carbonate compounds with compounds that react to epoxides or in a chemically similar manner in the context of the present invention (cyclic carbonates), particularly those which bear —OH, —COOH, —SH, $NH_2$ and similar groups or derivatives thereof—for example, appropriately functionalized, preferably multiply appropriately functionalized linear or branched, saturated or partially unsaturated, cyclic or linear (hetero)alkyls and (hetero)aryls—yields the desired alkenyl ether polyols.

Examples of compounds having at least one of the groups —OH, —COOH, —SH, $NH_2$ and derivatized forms thereof but no alkenyl ether groups include but are not limited to glycols, polyglycols, glycine, glycerol, hexamethylenediamine, 1,4-butanediol, and 1,6-hexanediol.

The alkenyl ether polyols that can be manufactured or obtained by means of the described methods are also the object of the invention. In various embodiments, they are compounds of formulas (I), (Ia), and (V), as defined above.

In various embodiments of the alkenyl ether polyols of formula (I), (1) m=1; R and R' are H or R is H and R' is methyl; $R_1$ is $C_{1-10}$ alkylenyl, particularly $C_{1-6}$ alkylenyl, X is O, A, and B are $CH_2$, n and o are 1 or 0 and p is 0, where n+o=1, and $R_2$ is an organic residue that is substituted with —OH or bears another residue of the formula

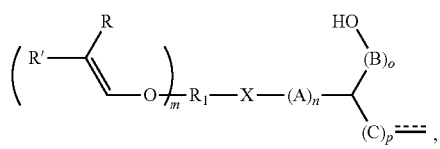

where $R_1$, m, R, R', A, B, C, n, o, and p are as defined above; or (2) m=1; R and R' are H or R is H and R' is methyl; $R_1$ is $C_{1-10}$ alkylenyl, particularly $C_{1-6}$ alkylenyl, X is $NR_x$, A and B are $CH_2$, n and o are 1 or 0 and p is 0, where n+o=1, $R_x$ is H or

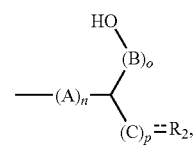

where A, B, C, n, o, and p are as defined above; and $R_2$ is an organic residue as defined above which, when $R_X$ is H, is substituted with —OH or bears another residue of the formula

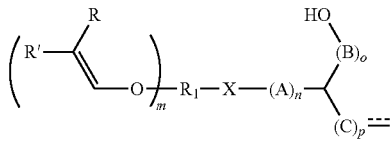

where $R_1$, m, R, R', A, B, C, n, o, and p are as defined above; or (3) m=1; R and R' are H or R is H and R' is methyl; $R_1$ is $C_{1-10}$ alkylenyl, particularly $C_{1-6}$ alkylenyl, X is OC(=O)O, A and B are $CH_2$, n and o are 1 or 0 and p is 0, where n+o=1, and $R_2$ is an organic residue that is substituted with —OH or bears another residue of the formula

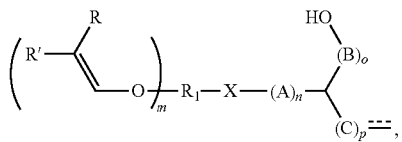

where $R_1$, m, R, R', A, B, C, n, o, and p are as defined above; or (4) m=1; R and R' are H or R is H and R' is methyl; $R_1$ is $C_{1-10}$ alkylenyl, particularly $C_{1-6}$ alkylenyl, X is $NR_xC$(=O)O, A and B are $CH_2$, n and o are 1 or 0 and p is 0, where n+o=1, $R_x$ is H or

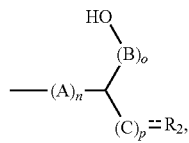

where A, B, C, n, o, and p are as defined above; and $R_2$ is an organic residue as defined above which, when $R_x$ is H, is substituted with —OH or bears another residue of the formula

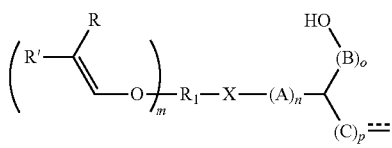

where $R_1$, m, R, R', A, B, C, n, o, and p are as defined above.

In the embodiments cited above, $R_2$ is preferably bonded via a single bond and can, for example, be a heteroalkyl residue, particularly an alkyl ether residue with 2 to 10 carbon atoms. For example, residues of formula —$CH_2$—O—$(CH_2)_4$—O—$CH_2$— (if $R_2$ bears two alkenyl ether residues of the above formula) or —$CH_2$—O—$CH(CH_3)_2$ are suitable.

In various embodiments of the alkenyl ether polyols of formula (V), (1) m=1; R and R' are H or R is H and R' is methyl; $R_1$ is —$(CH_2)_{1-10}$—O—$CH_2$—, particularly $(CH_2)_{1-6}$—O—$CH_2$—, X is O, A and B are $CH_2$, s and t are 1 or 0, where s+t=1, and $R_3$ is an organic residue that is substituted with —OH or bears another residue of the formula

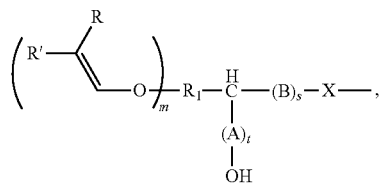

where $R_1$, m, R, R', A, B, s, and t are as defined above; or (2) m=1; R and R' are H or R is H and R' is methyl; $R_1$ is —$(CH_2)_{1-10}$—O—$CH_2$—, particularly $(CH_2)_{1-6}$—O—$CH_2$—, X is $NR_z$, A and B are $CH_2$, s and t are 1 or 0, where s+t=1, $R_z$ is H or

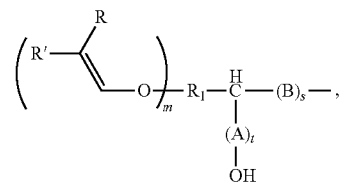

where A, B, m, s and t are as defined above; and $R_3$ is an organic residue as defined above which, if $R_z$ is H, is substituted with —OH or bears another residue of the formula

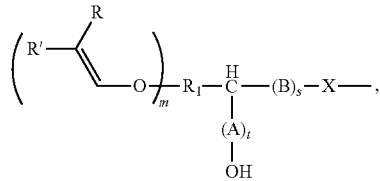

where $R_1$, m, R, R', A, B, s, and t are as defined above; or (3) m=1; R and R' are H or R is H and R' is methyl; $R_1$ is —$(CH_2)_{1-10}$—O—$CH_2$—, particularly $(CH_2)_{1-6}$—O—$CH_2$—, X is OC(=O), A and B are $CH_2$, s and t are 1 or 0, where s+t=1, and $R_3$ is an organic residue that is substituted with —OH or bears another residue of the formula

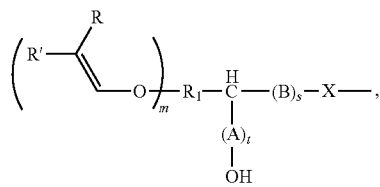

where $R_1$, m, R, R', A, B, s, and t are as defined above; or (4) m=1; R and R' are H or R is H and R' is methyl; $R_1$ is —$(CH_2)_{1-10}$—O—$CH_2$—, particularly $(CH_2)_{1-6}$—O—$CH_2$—, X is OC(=O)$NR_z$, A and B are $CH_2$, s and t are 1 or 0, where s+t=1, $R_z$ is H or

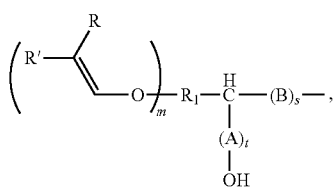

where A, B, m, s and t are as defined above; and $R_3$ is an organic residue as defined above which, if $R_2$ is H, is substituted with —OH or bears another residue of the formula

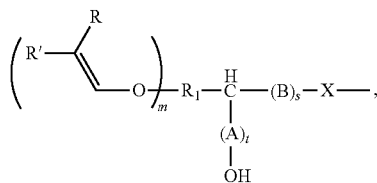

where $R_1$, m, R, R', A, B, s, and t are as defined above.

In the abovementioned embodiments of the compounds of formula (V), $R_3$ is a heteroalkyl residue, for example, particularly a (poly)alkylene glycol, such as particularly polypropylene glycol, or a $C_{1-10}$ alkyl- or alkylenyl residue.

The individual steps of the method according to the invention for manufacturing compounds (I) or (V) can be carried out using the methods that are commonly used for such reactions. For this purpose, the reaction partners, optionally after activation (for example, manufacture of alcoholates through conversion with sodium) are brought into contact with one another and converted, optionally under an inert gas atmosphere and with temperature control.

The alkenyl ether polyols that can be manufactured by means of the method according to the invention are suitable precursors for the synthesis of UV-curable oligomers or polymers by means of polyaddition or polycondensation reactions, particularly for the synthesis of UV-curable polyesters, polyethers, polyurethanes, and polyureas, especially preferably UV-curable polyurethanes. The use thereof in such syntheses and methods for the manufacture of such polymers using the described alkenyl ether polyols are additional aspects of the present invention. In particular, the alkenyl ether polyols manufactured according to the invention are suitable for the manufacture of UV-curable polyurethane polymers, which can be obtained through conversion of at least one alkenyl ether polyol in terms of the present invention with a polyisocyanate.

Methods for manufacturing UV-curable polyurethane polymers are known from the prior art and are described, for example, in example 6 of the present invention.

Methods for the manufacture of UV-curable polyurethane polymers will be described in the following for the sake of example. As will readily be understood, the invention is not limited to such embodiments; rather, they are intended only to further illustrate this aspect of the invention.

Using the alkenyl ether polyols described herein, particularly the vinyl ether polyols, high-quality vinyl ether-functionalized polyurethanes (VEPUs) can be produced by introducing active side chains into the polymer backbone via the novel polyols. In one specific example, 4-hydroxybutyl vinyl ether (HVBE) can be deprotonated and converted with 1,4-butanediol diglycidyl ether (BDDGE) in order to produce the vinyl ether-functionalized diol (VEOH). During the ring-opening through the nucleophilic attacking of the alcoholate, each epoxy group produces a new hydroxyl group. The resulting VEOH is then converted with isophorone diisocyanate in order to produce the side chain vinyl ether-functionalized polyurethane prepolymer (sc-VEPU). The terminal isocyanate groups can then be converted with HBVE in order to also functionalize the end groups with vinyl ether groups. A more detailed description of the synthesis can be found in examples 6 and 7. The reaction sequence is shown schematically in FIG. 1.

Finally, the invention also relates to the polymers, particularly the UV-curable polyurethanes that can be manufactured by means of the alkenyl ether polyols described herein. These polyurethanes can also be used in the form of water-based dispersions (PUDs).

The alkenyl ether-functionalized polyols described herein enable the synthesis of novel polyurethanes (PUs) which can be crosslinked (cured) by means of a cationic polymerization mechanism with UV radiation. Such curing is different from known methods for curing UV-curable polyurethanes, which are based on radical polymerization (such as acrylate-functionalized polyurethanes, for example). Such radical mechanisms have the drawback that they are sensitive to oxygen, that is, the presence of oxygen can inhibit the reaction, which constitutes a severe disadvantage for thin-layer applications and coatings.

Moreover, cationic UV curing makes it possible to provide "dark cure" characteristics; that is, after a short pulse of radiation, which is necessary for activation and initiates the polymerization or curing, the reaction proceeds without further radiation, i.e., independently of the UV radiation source. After it is started, the reaction can thus continue in the dark (=dark curing) or on a production line, which is a substantial advantage particularly for adhesive applications, e.g., in fully automated processes.

One advantage of the polymers manufactured using the alkenyl ether polyols described herein thus lies in the chemical reactivity of the alkenyl ether functionalization. Besides the possibility for UV curing already described, other reactions are also possible, such as the addition of thiols as another possibility for crosslinking.

Another advantage is that the described alkenyl ether polyols enable the controlled synthesis of polymers with a predefined proportion of UV-curable alkenyl ether groups. Known UV-curable polymers often contain terminal vinyl ether groups and are manufactured by capping the end groups with vinyl ethers. Due to the limited number of end groups, typically only 2, such polymers are not able to yield polymer systems with high crosslink densities or clear changes in the mechanical moduli after curing. The alkenyl ether polyols described herein therefore represent an alternative to the previously used monofunctional, commercially available vinyl ether-functionalized alcohols, such as, for example, 4-hydroxybutyl vinyl ether, cyclohexanedimethanol monovinyl ether, or 2-hydroxyethyl vinyl ether, which can be used as end group capping means. Due to the higher concentration and resulting tighter crosslink density, the curing is associated with a clearer change in the mechanical characteristics in comparison to terminally functionalized vinyl ether polyurethanes. In this way, tack-free films with shear moduli that are higher by orders of magnitude can thus be obtained.

The alkenyl ether polyols, particularly the vinyl ether polyols that are described herein, can therefore be used in addition or as an alternative to known polyols for the synthesis of polymers, particularly polyurethanes. Known polyols that are used for PU synthesis include but are not limited to polyether and polyester polyols, for example. For the polyurethane synthesis, the polyols or mixtures of polyols containing the described alkenyl ether polyols are converted with polyisocyanates, typically in molar excess. The reaction takes place under inherently known conditions, i.e., at elevated temperature and optionally in the presence of a catalyst. Depending on the quantity of alkenyl ether polyol used, the polyurethane (pre)polymers have the desired density of crosslinkable alkenyl ether groups. Examples of polyurethanes synthesized in this way were already described above in connection with the claimed methods.

All of the embodiments disclosed herein in connection with the methods according to the invention for manufacturing the alkenyl ether polyols are likewise applicable to the described alkenyl ether polyols as such as well as to the use thereof, methods for the use thereof, the polymers synthesized therewith, and the uses thereof, and vice versa.

The invention will be illustrated below on the basis of examples, which are not to be construed as a limitation.

EXAMPLES

Materials Used:

4-hydroxybutyl vinyl ether (HBVE) (BASF) and 3-aminopropyl vinyl ether (APVE) (BASF) were stored over molecular sieve 4 Å.

Sodium (Merck) was washed in dry diethyl ether and cut into pieces.

1,4-butanediol diglycidyl ether (BDDGE, Sigma-Aldrich, 95%), 2,3-epoxy propanol (glydidol, glycid; Evonik), isopropyl glycidyl ether (IPGE, Raschig), epichlorohydrin (Solvay, 99.8%), isophorone diisocyanate (IPDI) (Merck, 99%), polypropylene glycol (PPG) (Dow Chemical, Voranol 2000 L, 2000 g/mol), 1-heptanol (Acros Organics, 98%), dimethyl tin dineodecanoate (Momentive, Fomrez catalyst UL-28), 4,4'-dimethyldiphenyl iodonium hexafluorophosphate (Omnicat 440, IGM 98%), hexamethylenediamine (99%, Merck), tetrabutylammonium bromide (TBAB, 99%, Acros Organics), and sodium hydroxide (Riedel-de-Häen, 99%) were used as received.

Example 1: Synthesis of a Vinyl Ether Polyol (VEOH)

139.51 g (1.2 mol) HBVE were readied in a 250 ml round-bottom flask. A dropping funnel with pressure equalization was connected and 24.78 g (0.12 mol) BDDGE readied therein. The entire apparatus was dried in a vacuum and flooded with nitrogen. 7.00 g (0.3 mol) of sodium were added. After the sodium had dissolved completely, BDDGE was added slowly. The temperature was controlled such that it did not exceed 50° C. After the addition of the BDDGE was completed, stirring was performed for a time period of 30 minutes at 50° C. 50 ml of water were added in order to hydrolyze the remaining alcoholate. The product was washed several times with saturated sodium chloride solution and water and reduced in a vacuum in order to remove residual reactant and water. Yield: 76%. $^1$H-NMR (CDCl$_3$, xy MHz): δ (pp)=1.6-1.8 (12H, mid-CH$_2$ butyl), 2.69 (2H, OH, H/D exchangeable), 3.4-3.55 (16H, CH$_2$—O—CH$_2$), 3.70 (4H, CH$_2$—O-vinyl), 3.94 (2H, CH—O), 3.98 (1H, CH$_2$=CH—O trans), 4.17 (1H, CH$_2$=CH—O cis), 6.46 (1H, CH$_2$=CH—O gemi).

Example 2

50.58 g (0.5 mol) APVE and 139.44 g (81.2 mol) IPGE were readied in a 250 ml round-bottom flask and heated to reflux. The progressing exothermic reaction was controlled such that a temperature of 175° C. was not exceeded. The reaction was cooled to room temperature, and after IR spectroscopy indicated the conversion of the desired quantity of epoxide, 20 ml of sodium hydroxide (1 mol/l) were added, and the emulsion was heated to 100° C. over a period of 30 min in order to hydrolyze the remaining epoxide residues. The organic phase was washed several times with water and dried under reduced pressure. Yield: 54%. $^1$H-NMR (CDCl$_3$, xy MHz): δ (pp)=1.15 (12H, CH$_3$), 1.82 (2H, mid-CH$_2$ propyl), 2.45-2.80 (6H, CH$_2$—N), 3.05-3.30 (2H, OH), 3.40 (4H, CH$_2$—O-isopropyl), 3.59 (2H, CH isopropyl), 3.73 (2H, CH$_2$—O-vinyl), 3.81 (2H, CH—OH), 3.99 (1H, CH$_2$=CH—O trans), 4.18 (1H, CH$_2$=CH—O cis), 6.45 (1H, CH$_2$=CH—O gemi).

Example 3

58.08 g (0.5 mol) HBVE were readied in a 250 ml round-bottom flask. A dropping funnel with pressure equalization was connected and 7.41 g (0.13 mol) glycidol readied therein. The apparatus was dried in a vacuum and flooded with nitrogen. 3.00 g (0.13 mol) of sodium were added. After the sodium had dissolved completely, glycidol was added slowly. The temperature was controlled such that it did not exceed 50° C. The mixture was stirred over a period of 20 min at 50° C. after the glycidol had been added completely. 50 ml of water were added in order to hydrolyze the remaining alcoholates. The product was washed several times with saturated sodium chloride solution and water and reduced in a vacuum in order to remove any residual reactant and water. Yield: 77%. $^1$H-NMR (CDCl$_3$, xy MHz): δ (pp)=1.6-1.8 (4H, mid-CH$_2$ Butyl), 3.40-3.75 (2H, CH$_2$—O-vinyl+2H, CH$_2$—O-glyceryl+1H, CH—OH+1H, CH$_2$—OH+O—CH$_2$—CHOH+2×1H, OH), 3.85 (1H, CH$_2$—OH), 3.99 (1H, CH$_2$=CH—O trans), 4.19 (1H, CH$_2$=CH—O cis), 6.47 (1H, CH$_2$=CH—O gemi), no remaining epoxide peaks were observed.

Example 4a: Synthesis of 4-Glycidyl Butyl Vinyl Ether (GBVE)

116.16 g (1 mol) HBVE and 10.51 (0.05 mmol) tetrabutylammonium bromide were readied in a 1 l round-bottom flask using a dropping funnel with pressure equalization. A mixture of 300 ml toluene and 300 ml 50% aqueous sodium hydroxide solution were added. The reaction mixture was cooled with an ice bath and stirred rapidly. 148.16 g (2 mol) epichlorohydrin were added slowly, and the resulting emulsion was stirred over a period of 16 h at room temperature. The organic phase was washed several times with saturated sodium chloride solution and water. Solvent was removed under reduced pressure, and the product was purified by means of vacuum distillation in order to obtain a colorless liquid. Yield: 66%. $^1$H-NMR (CDCl$_3$, 400 MHz): δ (ppm)=1.6-1.8 (4H, mid-CH$_2$ butyl), 2.60 (1H, CH$_2$ epoxide), 2.79 (1H, CH$_2$ epoxide), 3.14 (1H, CH epoxide), 3.38 (1H, CH$_2$ glycidyl ether), 3.53 (2H, CH$_2$—O-glycidyl), 3.65-3.75 (2H, CH$_2$—O-vinyl+1H, CH$_2$ glycidyl ether), 3.97 (1H, CH$_2$=CH—O trans), 4.17 (1H, CH$_2$=CH—O cis), 6.47 (1H, CH$_2$=CH—O gemi).

Example 4b: Synthesis of 4-Glycidyl Carbonate Butyl Vinyl Ether (GBVE)

4-glycidyl carbonate butyl vinyl ether (GCBVE) was synthesized via CO$_2$ insertion in 17.22 g (0.1 mol) 4-glycidyl butyl vinyl ether in a process as described in the literature (Poly. Chem., 2013, 4, pp. 4545-4561). Yield: 87%. $^1$H-NMR (CDCl$_3$, 400 MHz): δ (ppm)=1.6-1.8 (4H, mid-CH$_2$ Butyl), 3.55 (2H, CH$_2$—O-glycidyl carbonate), 3.62 (1H, CH$_2$-carbonate), 3.70 (2H, CH$_2$—O-vinyl+1H, CH$_2$-carbonate), 3.99 (1H, CH$_2$=CH—O trans), 4.19 (1H, CH$_2$=CH—O cis), 4.39 (1H, CH$_2$ carbonate), 4.50 (1H, CH$_2$ carbonate), 4.82 (1H, CH carbonate), 6.46 (1H, CH$_2$=CH—O gemi), 2.5-3.5 (CH$_2$/CH epoxide). Integration shows <2% remaining epoxy.

Example 5: Polyol Synthesis Through Ring-Opening of GCBVE with Hexamethylenediamine 10.81 g (50 mmol) GCBVE and 2.95 g (25 mmol) hexamethylenediamine were readied in a round-bottom flask and heated for 9 h to 80° C. Conversion was observed through disappearance of the carbonate-C=O valence vibration bands in the IR spectrum. Yield: quantitative.

Example 6: Synthesis of Vinyl Ether-Functionalized Polyurethanes

The polyurethanes were synthesized in batches of 15-40 g each. The stoichiometry was calculated such that an NCO-terminated prepolymer was obtained that had a number-average molecular weight of M$_n$=5000 g/mol. The polyols were dried in a small round-bottom flask in a vacuum at 75° C. The isocyanate compounds were then added at 40° C. A sample of the mixture was removed for IR-spectroscopic investigations. The bands corresponding to N=C=O valence vibration at approximately 2550 cm$^{-1}$ was integrated and correlated with the original concentration of the isocyanate groups. The catalyst (50 mg/100 g product, as 50% solution in dry acetone) was then added, and the mixture was carefully heated to 80° C. After one hour of reaction time, an aliquot was removed in order to confirm the desired isocyanate concentration using IR spectroscopy. 90% of the stoichiometric quantity of the end-capping agent was added in order to avoid an excess of hydroxyl groups in the product and, after 30 min, another sample was removed in order to confirm the almost complete conversion of the isocyanate by means of IR spectroscopy. The product was then diluted with dry acetone to 50% polyurethane content. Yield: 95%.

Example 7: Synthesis of a Vinyl Ether-Functionalized Polyurethane 10.00 g of the vinyl ether polyol synthesized in example 1 were degassed under reduced pressure at 75° C. At 40° C., 5.82 g isophorone diisocyanate (Merck, 99%) and 0.0162 g Fomrez catalyst UL-28 (Momentive) were then added, and the mixture was heated slowly to 80° C. Side chain vinyl ether-functionalized polyurethane prepolymer (sc-VEPU) was obtained. After 1 h, 0.62 g 4-hydroxybutyl vinyl ether were added, and the reaction mixture was stirred for another 30 minutes in order to also convert the terminal isocyanate groups with HBVE, thereby producing additional terminal vinyl ether groups. The synthesis is shown schematically in FIG. 1. At Mn=5000 g/mol, an average vinyl ether functionality of about 16.5 was obtained.

For purposes of comparison, a vinyl ether-terminated polyurethane (t-VEPU) and an inactive alkyl-terminated polyurethane (i-PU) was synthesized from IPDI and polypropylene glycol (PPG) (Dow Chemical, Voranol 2000 L, 2000 g/mol) using 1-heptanol or HVBE as end group capping means. For t-VEPU, a vinyl ether functionality of 2 was thus obtained.

Curing was performed as follows: 1.98 g of the polyurethane functionalized with vinyl ether side chains (sc-VEPU) were mixed with 0.02 g Omnicat 440 (IGM) and 2 g acetone (solvent), with the latter being removed subsequently under reduced pressure. The formulation was applied as a thin film onto a surface and cured under UV irradiation (Omnicure S2000SC, 10 s) in order to yield a tack-free film. The sc-VEPU film applied to a glass surface and cured is shown in FIG. 2b. The figure shows that colorless and highly transparent films can be produced in this way.

Example 8: Synthesis of a Hydrated Vinyl Ether Polyol (hsc-VEPU)

A solution of the VEOH from example 1 (0.02 mol/L) in methanol was hydrated using an HC-2.SS H-Cube device for continuous hydration (ThalesNano). The required quantity of hydrogen was produced through electrolysis of water and then dried. The solution of the reactant was then loaded with hydrogen under a pressure of 20 bar at 25° C. in a mixing chamber and fed at a constant flow rate of 1.2 ml/min through the reaction chamber, which contained a 10% Pd/C (CatCart 30) catalyst cartridge. Methanol was removed under reduced pressure. Yield: 98%. $^1$H-NMR (CDCl$_3$, 400 MHz): δ (ppm)=1.2 (6H, CH$_3$), 1.6-1.8 (12H, mid-CH$_2$ butyl), 3.4-3.55 (24H, CH$_2$—O—CH$_2$), 3.93 (2H, CH—O), 4.19 & 6.46 (residual vinyl ether, peak integration showed 1-2% residue). The synthesis is shown schematically in FIG. 1.

4-hydroxybutyl vinyl ether was then added, and the reaction mixture was stirred for another 30 minutes in order to convert the terminal isocyanate groups with HBVE, thereby producing terminal vinyl ether groups. For hsc-VEPU, a vinyl ether functionality of 2 was thus obtained.

Example 9: UV-NIR Rheometry

The simultaneous measurement of the viscoelastic characteristics and the absorption of near-infrared (NIR) spectra after UV initiation was carried out using a rheometer and an experimental setup as described by Scherzer (Scherzer, T.; Schröder, M. W. *Proc. RadTech Europe* 2009 *Conference* 2009). An Anton Paar MCR 302 rheometer was used in conjunction with a Bruker MPA FT-NIR spectrometer and an Omnicure S 2000 SC light source, with both being triggered by the Rheometer software. The experimental setup is shown schematically in FIG. 2a. The sample was placed in the center of the quartz base plate, and an aluminum plate having a 20 mm diameter was used as a movable spindle with an initial gap of 0.3 mm. A normal force of zero was used for the automatic gap control during shrinking of the sample in order to prevent delamination. The mechanical data were obtained via oscillation of the spindle. An ascending measurement profile was used in order ensure linear viscoelastic behavior and to remain within the limits of the instrument, since the sample moduli increase by several orders of magnitude during curing. Before UV irradiation, a sinusoidal tensile stress of 10% was applied for 30 s at a frequency of 10 Hz. During UV irradiation, which was performed through the transparent base plate, the tensile stress was reduced linearly within 10 seconds from 10% to 0.1% and mechanical data were recorded at a rate of 1 s$^{-1}$ (no ascending measurement profile was applied to the inactive heptanol-capped polyurethane). The UV light source was set such that it irradiated the sample for 10 seconds. The intensity of 2 mW cm$^{-2}$ UVC (189 mW cm$^{-2}$ UVA-C) on the surface of the quartz plate was checked regularly using a spectral radiometer (OpSyTec Dr. Göbel). After UV irradiation, the post-curing development was recorded for 200 s under a tensile stress of 0.1%. Several samples were then irradiated for an additional 10 s and the post-curing was recorded again. No attempt was made to removed dissolved gases from the samples, and the measurements were recorded under instrumental air atmosphere (H$_2$O: 1.1 mg/m$^3$). For purposes of comparison, an experiment was conducted under nitrogen atmosphere (N$_2$: <99.9996%, O$_2$: <0.5 ppm, H$_2$O: <1 ppm). The NIR spectra were recorded at a resolution of 16 cm$^{-1}$ at a constant recording rate of about 2 spectra s$^{-1}$. The relative vinyl ether concentration was calculated from the integrated peak area of the C=C stretching vibration at approximately 6200 cm$^{-1}$. The mean value for this peak in the spectra before irradiation was set at 100%.

FIG. 2c shows the rheometric plots for the synthesized polyurethanes i-PU, t-VEPU, sc-VEPU, and hsc-VEPU (see examples 6-8). The irradiation period of 10 seconds is designated by the region in the diagram that is shaded in gray. As expected, i-PU did not exhibit any increase in the storage modulus. The slight decrease in the storage modulus upon irradiation of all of the samples is likely a thermal effect due to light absorption or the breaking-down of the photoinitiator, it being possible for cleaved-off initiator fragments to act as softeners. The t-VEPU exhibits a delay of about 10 s between irradiation and the initial quick increase in the storage modulus. In the case of the curing of the terminally functionalized PUs under dry nitrogen in order to rule out any influence of oxygen or air humidity, no improvement was observed. The delay can likely be attributed to a relatively slow initial reaction, and a similar behavior was observed for the side chain-functionalized samples. Due to its chemical structure, the t-VEPU has a relatively low initial storage modulus, since it has a small quantity of urethane bonds and approximately 82 wt % PPG segments. The storage modulus can therefore increase by several orders of magnitude during UV irradiation, but it does not exceed the Dahlquist criterion, which indicates the limit value over which tack-free films are obtained (Dahlquist, C. A., Tack. In Adhesion Fundamentals and Practice, 1969; pp. 143-151). The stickiness of the cured t-VEPU shows that the flexible polymer chains cannot be crosslinked strongly enough via the terminal, reactive groups. The first harmonic of the stretch vibration of the vinyl ether C=C double bond can be found in the NIR spectrum as a relatively sharp absorption band at 6200 cm$^{-1}$. (Workman, J.; Weyer, L., Alkenes and Alkynes. In Practical Guide and Spectral Atlas for Interpretive Near-Infrared Spectroscopy, Second Edition, CRC Press: 2012; pp 33-38.; Scherzer, T.; Buchmeiser, M. R. Macromolecular Chemistry and Physics 2007, 208, (9), 946-954). The analysis of the integrated peak area shows the consumption of the vinyl ether. Due to the low concentration of end groups, however, the signal/background ratio was too low in order to reliably calculate the conversion.

The hsc-VEPU, which also bears only terminal vinyl ether groups, was prepared in order to study the influence of the polyurethane backbone. The short polyol structure of the hydrated VEOH shifts the composition in the direction of a higher content of hard urethane segments, which leads to stronger intermolecular interactions and higher initial viscosity. Accordingly, the storage modulus is significantly higher at the beginning and develops at a lower rate after UV initiation. This can be attributed to reduced mobility on the part of the functional groups and slower diffusion kinetics. Macromonomers in particular are strongly influenced by increased viscosities. On the other hand, the slower reaction clearly shows the post-curing. Even though the cured hsc-VEPU exhibits a greater storage modulus than t-VEPU, it is still slightly tacky.

By contrast, the high-quality vinyl ether-functionalized sc-VEPU cures with a comparable backbone structure to a tack-free film and, as a direct consequence of the high crosslinking rates that can be achieved, exhibits an outstanding storage modulus, which is important particularly for its suitability as a building material.

FIG. 3 shows the curing of side chain-functionalized polyurethane (sc-VEPU) over the development of the storage moduli and relative vinyl ether contents by means of in-situ NIR measurement at different temperatures (25° C., 40° C., and 60° C.), with the measurement being accelerated at higher temperatures. At 25° C. and 40° C. conversion rates of approximately 45% and 75% are achieved after a first initiation. A second initiation can increase the conversion to approximately 70% and 90%. It is assumed that the active chain ends in crosslinked regions are enclosed and therefore become inaccessible for residual vinyl ether groups. The second initiation produces new polymerizable groups that are then less crosslinked and more mobile at this point in time. One noteworthy and mechanistically important observation is that, at 60° C., the sc-VEOH polymerization takes place very quickly to nearly complete conversion. A strong influence from the termination can therefore be ruled out, since the corresponding termination reactions have higher activation energies than the ongoing reaction and are thus accelerated more strongly at elevated temperatures.

Slightly negative values for the residual vinyl ether concentration in FIG. 3 result from the complete disappearance of the peak in a convex region of the spectra (see FIG. 4). FIG. 4 shows the NIR spectra of the sc-VEPU (example 7) with UV-initiated curing at 60° C. The NIR spectra were recorded using the previously described UV-NIR rheometer setup, and the sample was irradiated for 30-40 s. The increasing overall intensity at this point in time correlates with the shrinking of the sample by 3.7%. The peak at 6200 cm$^{-1}$ is correlated with the first harmonic of the C—H axial vibration and decreases during polymerization after UV initiation.

The results of the measurements are shown in FIGS. 5-8. FIG. 5 shows the IR spectrum for i-PU synthesis (inactive alkyl-terminated polyurethane). This polyurethane was synthesized starting from isophorone diisocyanate (IPDI) and polypropylene glycol (PPG) as specified in example 6 and terminated with 1-heptanol (FIG. 1). Spectra were recorded after the addition of the isocyanate (reactant), after one hour of reaction time (prepolymer), and after 30 min after the addition of the terminating agent (terminated). Several structurally relevant peaks are correlated. The integrated peak areas that correspond to the N=C=O valence vibration at 2550 cm$^{-1}$, as well as the associated molar quantities that were calculated from the stoichiometry, are as follows:

|  | n(NCO) | | A(NCO) | |
| --- | --- | --- | --- | --- |
|  | [mmol] | % | [Counts] | % |
| Reactant | 45.0 | 100 | 9567 | 100 |
| Prepolymer | 14.3 | 32 | 3005 | 31 |
| Terminated | 1.4 | 3 | 276 | 3 |

FIG. 6 shows the IR spectrum of the t-VEPU synthesis (vinyl ether-terminated polyurethane). The polyurethane was synthesized starting from IPDI and PPG as specified in example 6 and terminated with 4-hydroxybutyl vinyl ether (FIG. 1). Spectra were recorded after the addition of the isocyanate (reactant), after one hour of reaction time (prepolymer), and after 30 min after the addition of the terminating agent (terminated). Several structurally relevant peaks are correlated. The integrated peak areas that correspond to the N═C═O valence vibration at 2550 cm$^{-1}$, as well as the associated molar quantities that were calculated from the stoichiometry, are as follows:

|  | n(NCO) | | A(NCO) | |
| --- | --- | --- | --- | --- |
|  | [mmol] | % | [Counts] | % |
| Reactant | 45.0 | 100 | 9839 | 100 |
| Prepolymer | 14.3 | 32 | 3022 | 31 |
| Terminated | 1.4 | 3 | 358 | 4 |

FIG. 7 shows the IR spectrum of the sc-VEPU synthesis (side chain vinyl ether-functionalized polyurethane). The polyurethane was synthesized starting from IPDI and VEOH as specified in example 7 and terminated with 4-hydroxybutyl vinyl ether (FIG. 1). Spectra were recorded after the addition of the isocyanate (reactant), after one hour of reaction time (prepolymer), and after 30 min after the addition of the terminating agent (terminated). Several structurally relevant peaks are correlated. The C═C axial vibration band of the vinyl ether at 1615 cm$^{-1}$ clearly shows a relatively high vinyl ether concentration and confirms that no consumption of the vinyl ether occurs under synthesis conditions. The integrated peak areas that correspond to the N═C═O valence vibration at 2550 cm$^{-1}$, as well as the associated molar quantities that were calculated from the stoichiometry, are as follows:

|  | n(NCO) | | A(NCO) | |
| --- | --- | --- | --- | --- |
|  | [mmol] | % | [Counts] | % |
| Reactant | 52.4 | 100 | 26020 | 100 |
| Prepolymer | 6.3 | 12 | 4600 | 18 |
| Terminated | 0.6 | 1 | 294 | 1 |

It can be seen that the reaction can be controlled well under the given conditions.

FIG. 8 shows the IR spectrum of the hsc-VEPU synthesis (hydrated side chain vinyl ether-functionalized polyurethane). The polyurethane was synthesized starting from IPDI and VEOH as specified in example 7 and terminated with 4-hydroxybutyl vinyl ether. It was then hydrated (FIG. 1). Spectra were recorded after the addition of the isocyanate (reactant), after one hour of reaction time (prepolymer), and after 30 min after the addition of the terminating agent (terminated). Several structurally relevant peaks are correlated. The C═C axial vibration band of the vinyl ether at 1615 cm$^{-1}$ shows that the hsc-VEPU has only slight traces of residual vinyl ether groups. The integrated peak areas that correspond to the N═C═O valence vibration at 2550 cm$^{-1}$, as well as the associated molar quantities that were calculated from the stoichiometry, are as follows:

|  | n(NCO) | | A(NCO) | |
| --- | --- | --- | --- | --- |
|  | [mmol] | % | [Counts] | % |
| Reactant | 52.4 | 100 | 25601 | 100 |
| Prepolymer | 6.3 | 12 | 3277 | 13 |
| Terminated | 0.6 | 1 | 201 | 1 |

Figure 1:
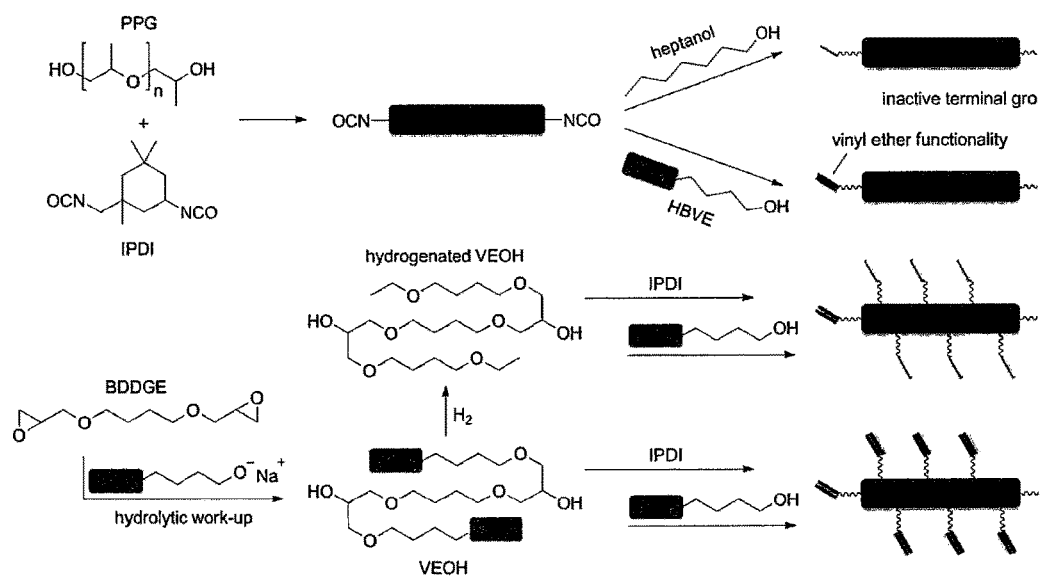
FIG. 1 schematically illustrates one scheme for synthesizing vinyl ether-functionalized polyurethanes (VEPUs).
Figure 2A:
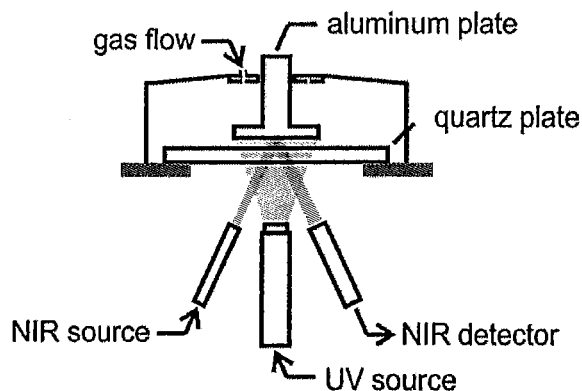
FIG. 2A schematically illustrates a setup to simultaneously measure the viscoelastic characteristics and the absorption of near-infrared (NIR) spectra after UV initiation of a composition.
Figure 2B:
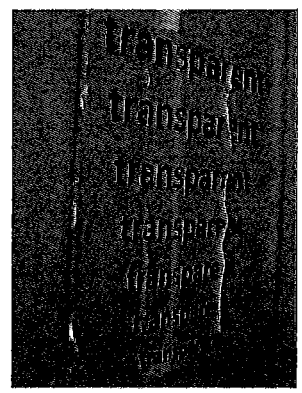
FIG. 2B shows a sc-VEPU film applied to a glass surface and cured to produce a colorless and highly transparent film.
Figure 2C:
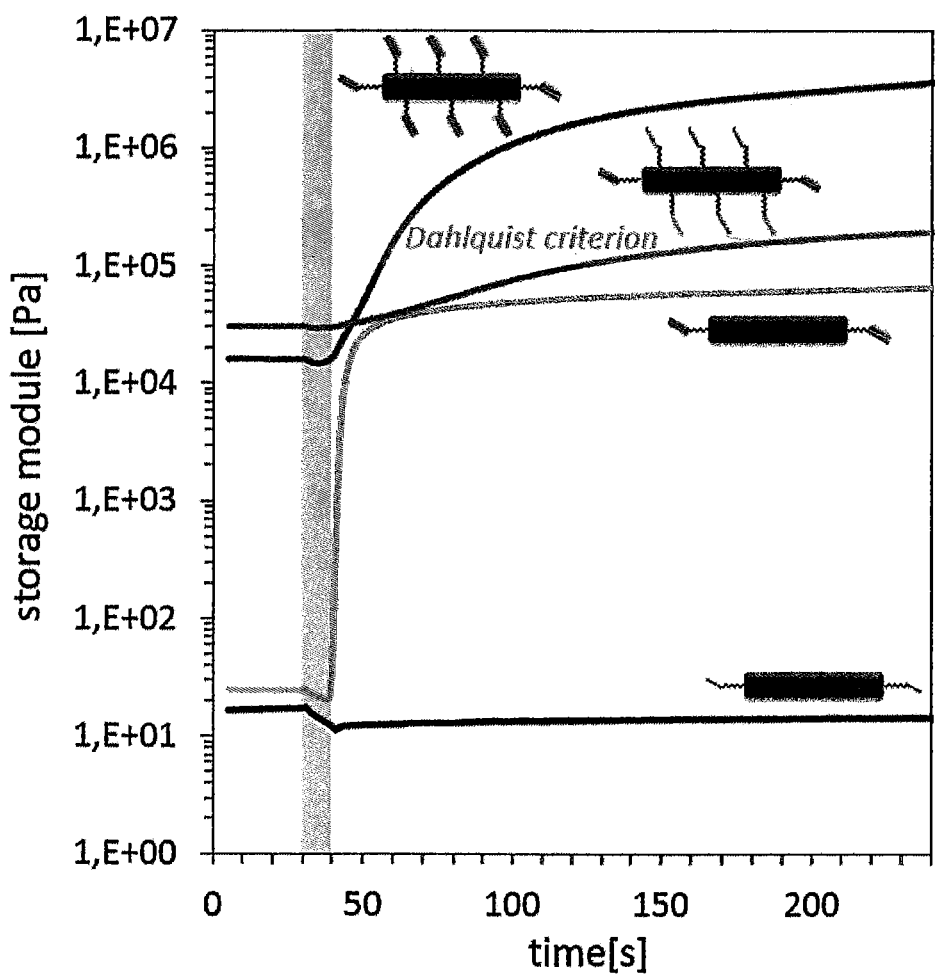
FIG. 2C shows rheometric plots for the synthesized polyurethanes i-PU, t-VEPU, sc-VEPU, and hsc-VEPU.
Figure 3:
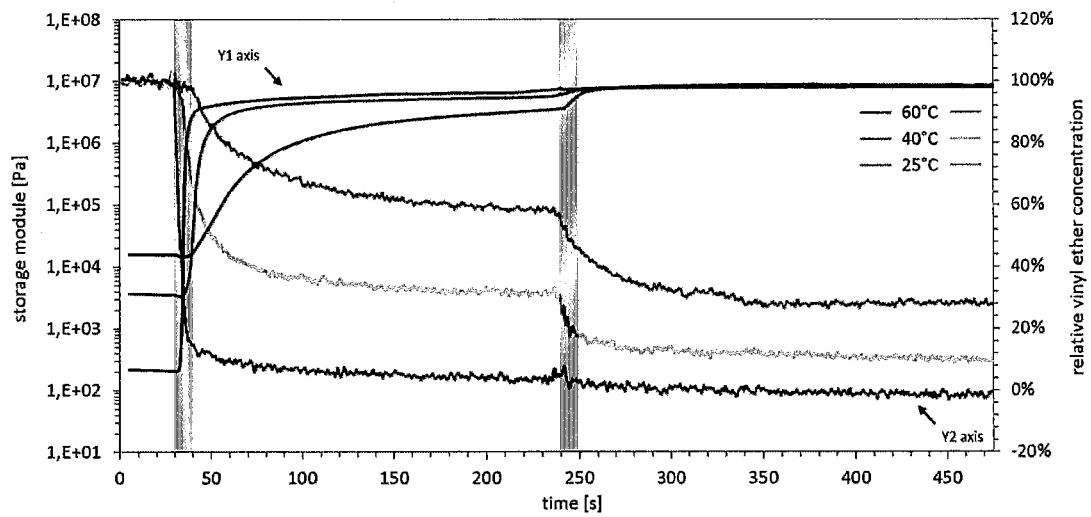
FIG. 3 shows the curing of side chain-functionalized polyurethane (sc-VEPU) over the development of the storage moduli and relative vinyl ether contents by means of in-situ NIR measurement at different temperatures (25° C., 40° C., and 60° C.).
Figure 4:
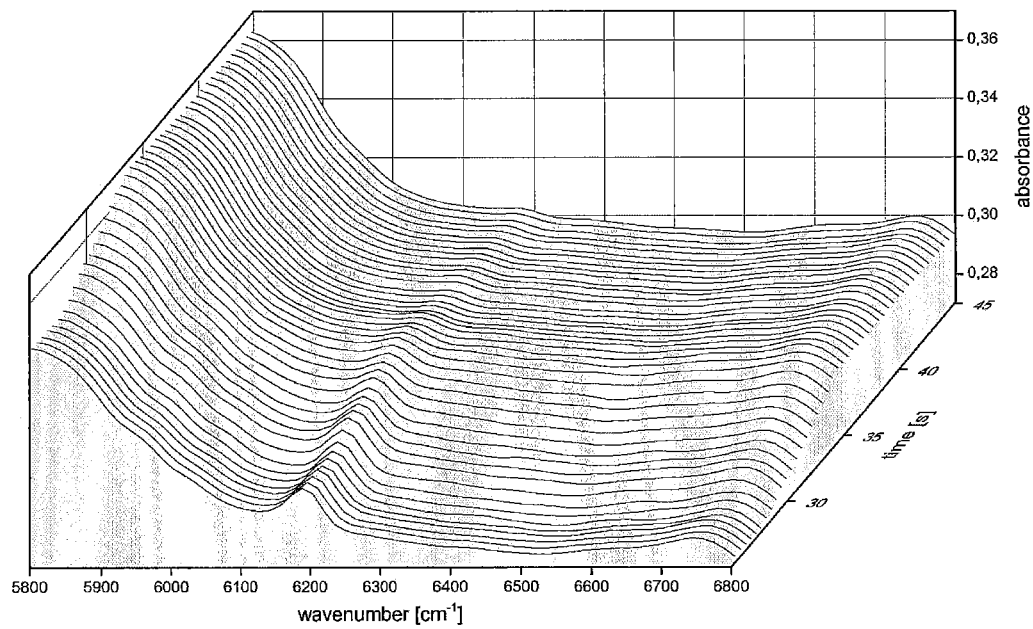
FIG. 4 shows the NIR spectra of the sc-VEPU (example 7) with UV-initiated curing at 60° C.
Figure 5:
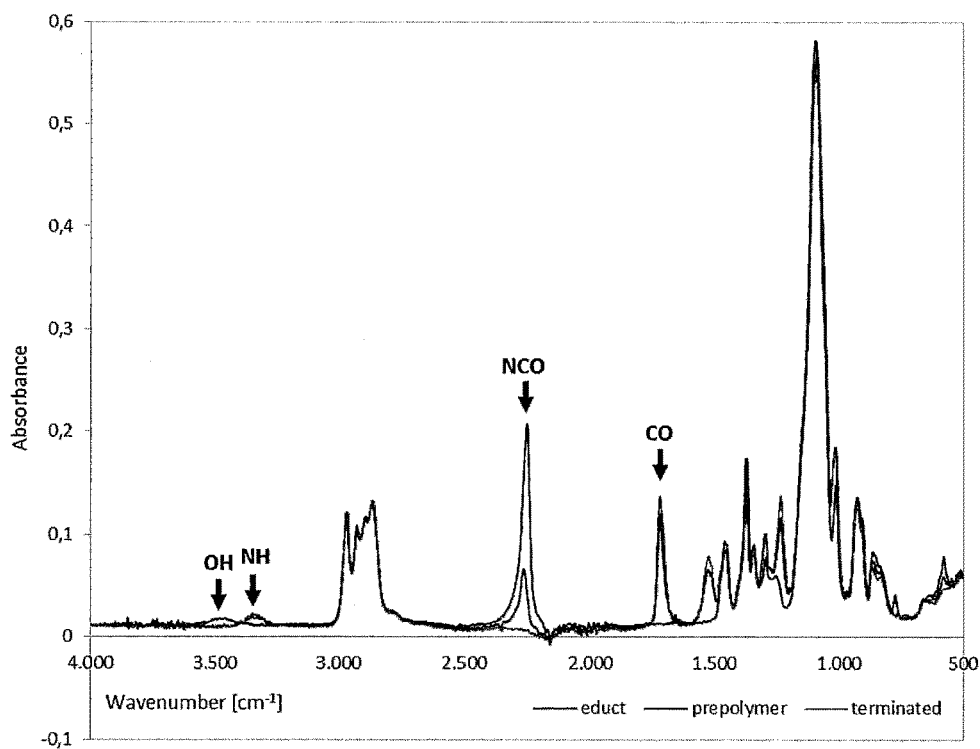
FIG. 5 shows the IR spectrum for i-PU synthesis (inactive alkyl-terminated polyurethane).
Figure 6:
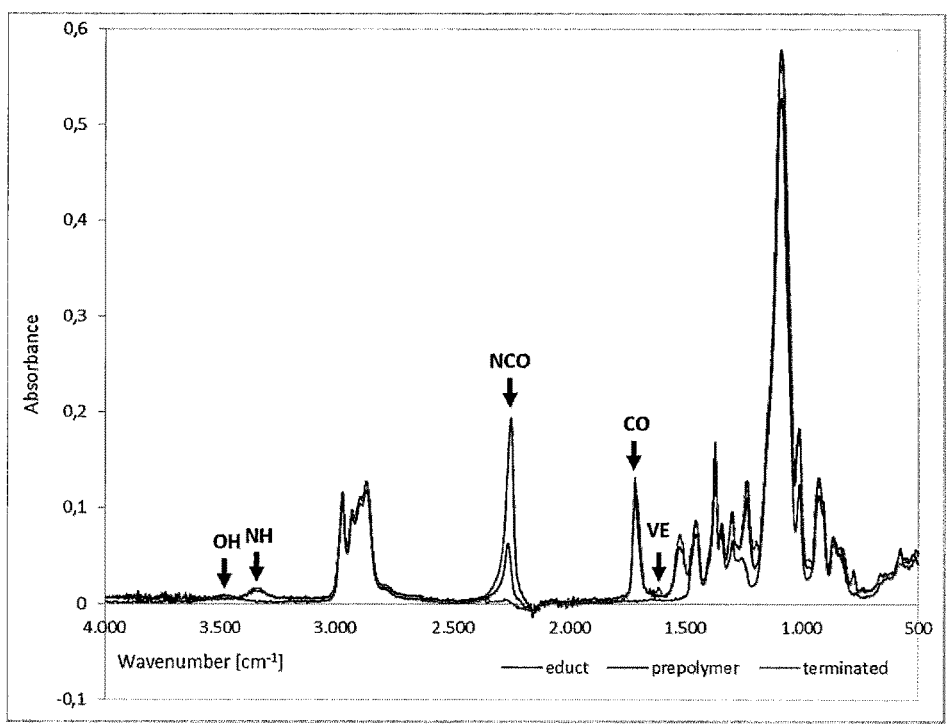
FIG. 6 shows the IR spectrum of the t-VEPU synthesis (vinyl ether-terminated polyurethane).
Figure 7:
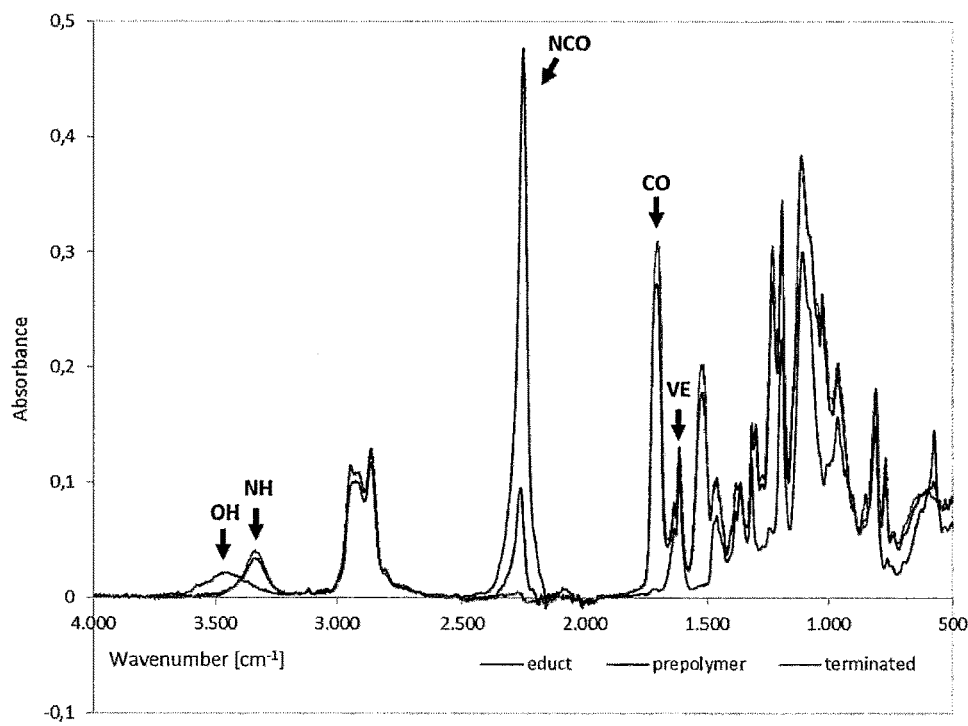
FIG. 7 shows the IR spectrum of the sc-VEPU synthesis (side chain vinyl ether-functionalized polyurethane).
Figure 8:
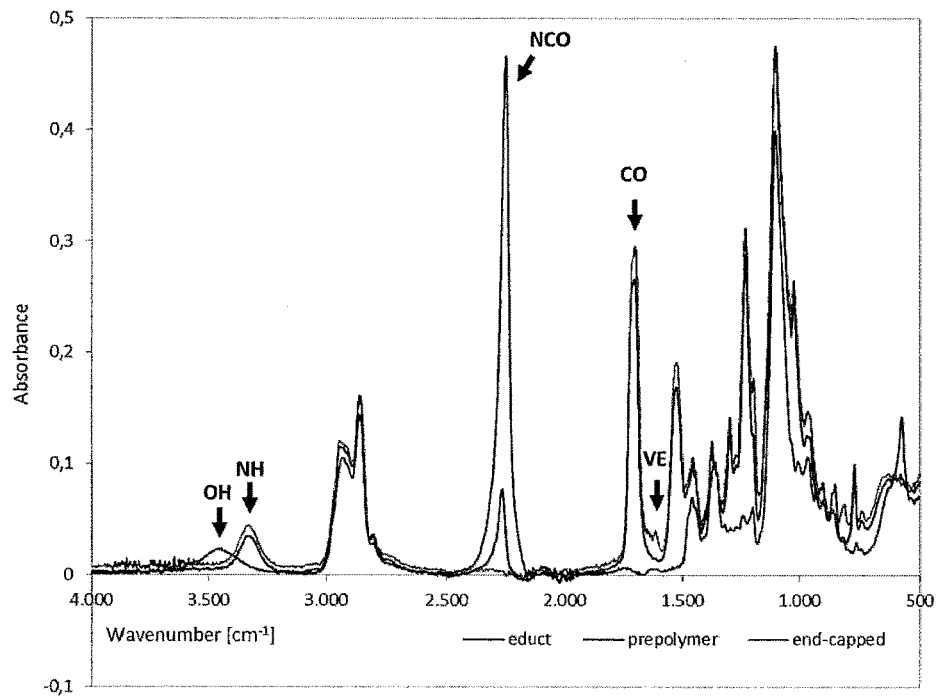
FIG. 8 shows the IR spectrum of the hsc-VEPU synthesis (hydrated side chain vinyl ether-functionalized polyurethane).

The invention claimed is:

1. A method for manufacturing an alkenyl ether polyol containing at least one alkenyl ether group and at least two hydroxyl groups (—OH), comprising:
    A) conversion of an alkenyl ether containing at least one alkenyl ether group and at least one functional group selected from —OH, —COOH, —SH, -NH$_2$ and derivatives thereof,
    with (i) an epoxide or (ii) a cyclic carbonate or derivative thereof; or
    B) conversion of an alkenyl ether containing at least one alkenyl ether group and at least one functional group selected from (i) epoxide groups and (ii) cyclic carbonate groups or derivatives thereof, with a thiol, a carboxylic acid, or an amine or derivative thereof; or
    C) conversion of an alkenyl ether containing at least one alkenyl ether group and at least one functional group selected from cyclic carbonate groups or derivatives thereof, with an alcohol.

2. The method as set forth in claim 1, wherein the alkenyl ether polyol is manufactured through conversion of an alkenyl ether containing at least one alkenyl ether group and at least one functional group selected from —OH, —COOH, —SH, -NH$_2$ and derivatives thereof with (i) an epoxide or (ii) a cyclic carbonate or derivative thereof, wherein:
    the alkenyl ether polyol is an alkenyl ether polyol of formula (I)

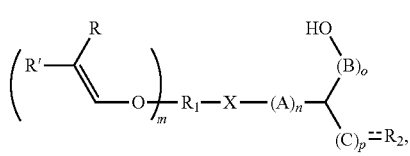 (I)

where
- R$_1$ is selected from a divalent organic residue; a divalent linear or branched, substituted or unsubstituted, alkyl with 1 to 20 carbon atoms; or a linear or branched, substituted or unsubstituted, heteroalkyl with 1 to 20 carbon atoms and at least one oxygen or nitrogen atom,
- R$_2$ is selected from an organic residue; an organic residue with at least one —OH group and/or 1 to 1000 carbon atoms; an optionally divalent or polyvalent, linear or branched, substituted or unsubstituted, alkyl with 1 to 20 carbon atoms; or a linear or branched, substituted or unsubstituted, heteroalkyl with 1 to 20 carbon atoms and at least one oxygen or nitrogen atom,
- X is O, S, C(=O)O, OC(=O)O, C(=O)OC(=O)O, NR$_x$, NR$_x$C(=O)O, NR$_x$C(=O)NR$_x$, or OC(=O)NR$_x$,
- each R and R' is selected independently from H, C$_{1-20}$ alkyl, and C$_{2-20}$ alkenyl; or one of R and R' is H and the other is C$_{1-4}$ alkyl; or both R and R' are H,
- each A, B, and C is independently selected from among CR"R"',
  - R" and R"' are selected independently from H, a functional group, an organic residue, C$_{1-20}$ alkyl; or R" and R"' together or with the carbon atom to which they are bonded are an organic residue; or two of R" and R"' that are bonded to neighboring carbon atoms form a bond together in order to form a double bond between the neighboring carbon atoms,
  - ═ is a single or double bond, and if it is a double bond, the carbon atom that is bonded to R$_2$ bears only one substituent R" or R"',
- m is an integer from 1 to 10, preferably 1,
- n, p, and o are each 0 or an integer from 1 to 10, and
- R$_x$ is H, an organic residue, or

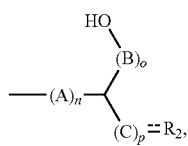

and if X is not NR$_x$ where

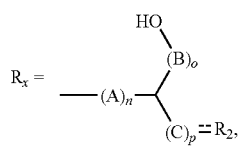

R$_2$ has at least one substituent that is selected from among —OH and

3. The method as set forth in claim 2 wherein n+p+o=1 or 2.

4. The method as set forth in claim 2, wherein the alkenyl ether, which contains at least one alkenyl ether group and at least one functional group selected from among —OH, —COOH, —SH, NH$_2$ and derivatives thereof, is an alkenyl ether of formula (II)

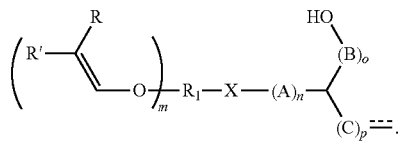 (II)

where
- R$_1$ is selected from a divalent organic residue; a divalent, linear or branched, substituted or unsubstituted, alkyl with 1 to 20 carbon atoms; or a linear or branched, substituted or unsubstituted, heteroalkyl with 1 to 20 carbon atoms and at least one oxygen or nitrogen atom,
- X$_1$ is a functional group selected from among OH, —COOH, —SH, —NHR$_y$ and derivatives thereof,
- R$_y$ is H or an organic residue,
- each R and R' is selected independently from among H, C$_{1-20}$ alkyl, and C$_{2-20}$ alkenyl; or one of R and R' is H and the other is C$_{1-4}$ alkyl; or both R and R' are H, and
- m is an integer from 1 to 10.

5. The method as set forth in claim 4, wherein in the alkenyl ether of formula (II),
- m is 1,
- X$_1$ is —OH or —NH$_2$,
- R$_1$ is selected from a divalent, linear or branched C$_{1-10}$ alkyl residue, ethyl, propyl, butyl, pentyl, or hexyl, and one of R and R' is H and the other is H or —CH$_3$.

6. The method as set forth in claim 1, wherein the epoxide is an epoxide of formula (III)

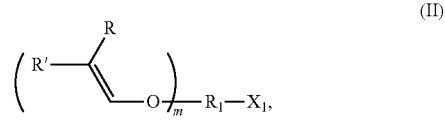 (III)

where R$_2$ is selected from an organic residue; an organic residue with at least one —OH group; an optionally divalent or polyvalent, linear or branched, substituted or unsubstituted, alkyl with 1 to 20 carbon atoms; or a linear or branched, substituted or unsubstituted, heteroalkyl with 1 to 20 carbon atoms and at least one oxygen or nitrogen atom, and
q is an integer from 1 to 10.

7. The method as set forth in claim 6, wherein:
- q is 1 or 2, and
- if q is 2, R$_2$ is —CH$_2$—O—C$_{1-10}$-alkylenyl-O—CH$_2$—; and if q is 1, R$_2$ is —CH$_2$—O—C$_{1-10}$-alkyl.

8. The method as set forth in claim 1, wherein the cyclic carbonate is an ethylene carbonate of formula (IV)

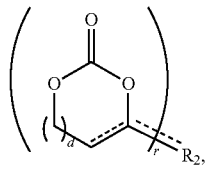
(IV)

where $R_2$ is selected from an organic residue; an organic residue with at least one —OH group; an optionally divalent or polyvalent, linear or branched, substituted or unsubstituted, alkyl with 1 to 20 carbon atoms; a linear or branched, substituted or unsubstituted, heteroalkyl with 1 to 20 carbon atoms and at least one oxygen or nitrogen atom; or a $C_{1-10}$ hydroxyalkyl,
⸺ is a single or double bond,
d is 0 or 1, and
r is an integer from 1 to 10.

9. The method as set forth in claim 4, wherein:
(i) $X_1$ is —$NH_2$ or a derivative thereof, and
q or r is 1; or
(ii) $X_1$ is —OH or a derivative thereof, and
q or r is 2.

10. The method as set forth in claim 1, wherein the alkenyl ether polyol is an alkenyl ether polyol of formula (V)

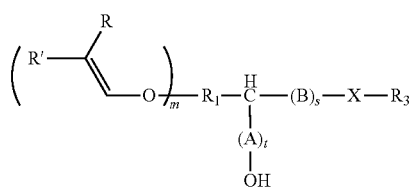
(V)

where
$R_1$ is selected from a divalent organic residue; a divalent linear or branched, substituted or unsubstituted, alkyl with 1 to 20 carbon atoms; or a linear or branched, substituted or unsubstituted, heteroalkyl with 1 to 20 carbon atoms and at least one oxygen or nitrogen atom,
$R_3$ is selected from an organic residue; an organic residue with 1 to 1000 carbon atoms; an optionally divalent or polyvalent, linear or branched, substituted or unsubstituted, alkyl with 1 to 20 carbon atoms; a linear or branched, substituted or unsubstituted, heteroalkyl with 1 to 20 carbon atoms and at least one oxygen or nitrogen atom; a (poly)alkylene glycol of the formula —O—[$CHR_aCH_2O$]$_b$—$R_b$, where b is 1 to 100, $R_a$ is H or a $C_{1-4}$ alkyl residue, $R_b$ is H; or

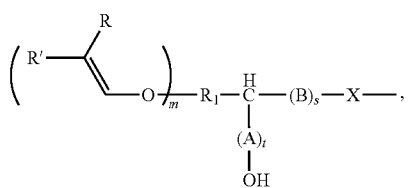

X is O, S, OC(=O), OC(=O)O, OC(=O)OC(=O), $NR_z$, $NR_zC(=O)O$, $NR_zC(=O)NR_z$, or OC(=O)$NR_z$,
each R and R' is selected independently from H, $C_{1-20}$ alkyl, $C_{2-20}$ alkenyl; or one of R and R' is H and the other is $C_{1-4}$ alkyl; or both R and R' are H,
each A and B is independently selected from among CR"R'",
R" and R'" are selected independently from H, a functional group, an organic residue, H and $C_{1-20}$ alkyl; or R" and R'" together or with the carbon atom to which they are bonded are an organic residue; or two of R" and R'" that are bonded to neighboring carbon atoms form a bond together in order to form a double bond between the neighboring carbon atoms,
m is an integer from 1 to 10,
s and t are each 0 or an integer from 1 to 10, where s+t=1 or 2, and
$R_z$ is H, an organic residue

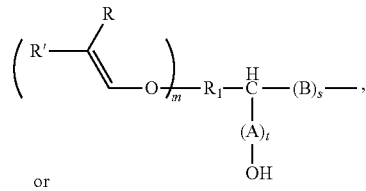

or and if X is not $NR_z$ where

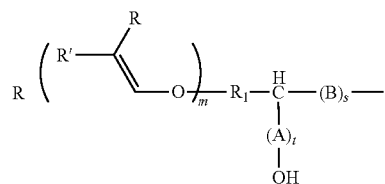

than $R_3$ has at least one substituent that is selected from among —OH and

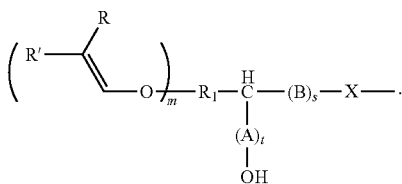

11. The method as set forth in claim 1, wherein the alkenyl ether, which contains at least one alkenyl ether group and at least one functional group selected from among (i) epoxide groups and (ii) cyclic carbonate groups or derivatives thereof, is an alkenyl ether of formula (VI) or (VII)

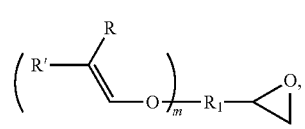
(VI)

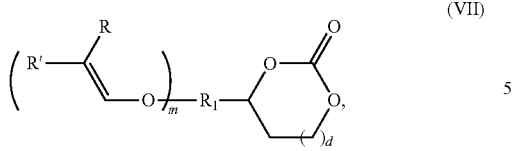

(VII)

where $R_1$ is selected from a divalent organic residue; a divalent linear or branched, substituted or unsubstituted alkyl with 1 to 20 carbon atoms; or a linear or branched, substituted or unsubstituted, heteroalkyl with 1 to 20 carbon atoms and at least one oxygen or nitrogen atom, each R and R' is selected independently from among H, $C_{1-20}$ alkyl, and $C_{2-20}$ alkenyl; or one of R and R' is H and the other is $C_{1-4}$ alkyl; or both R and R' are H, d is 0 or 1, and m is an integer from 1 to 10.

12. The method as set forth in claim 11, wherein in the alkenyl ethers of formula (VI) or (VII), $R_1$ is —$C_{1-10}$-alkylenyl-O—$CH_2$—.

13. The method as set forth in claim 11, wherein the alkenyl ether is converted with an alcohol, with the alcohol being a diol or polyol or a corresponding alcoholate.

14. The method as set forth in claim 11, wherein the alkenyl ether is converted with a polyalkylene glycol of the formula HO—[$CHR_aCH_2O$]$_b$—H, where $R_a$ is H or a $C_{1-4}$ alkyl residue and b is 1 to 100.

* * * * *